(12) United States Patent
Lee et al.

(10) Patent No.: US 10,416,833 B2
(45) Date of Patent: Sep. 17, 2019

(54) METHOD AND APPARATUS FOR DISPLAYING MEDICAL IMAGE

(71) Applicant: SAMSUNG ELECTRONICS CO., LTD., Suwon-si (KR)

(72) Inventors: Jun-ki Lee, Seoul (KR); Jun-sung Park, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 357 days.

(21) Appl. No.: 15/166,803

(22) Filed: May 27, 2016

(65) Prior Publication Data

US 2016/0349957 A1     Dec. 1, 2016

(30) Foreign Application Priority Data

May 28, 2015   (KR) .................. 10-2015-0075365

(51) Int. Cl.
| | | |
|---|---|---|
| *G06F 3/048* | (2013.01) | |
| *G06F 3/0481* | (2013.01) | |
| *G06F 19/00* | (2018.01) | |
| *G06F 3/0482* | (2013.01) | |
| *G06F 3/0484* | (2013.01) | |
| *G06F 3/0489* | (2013.01) | |
| *G06F 3/038* | (2013.01) | |

(52) U.S. Cl.
CPC .......... *G06F 3/04812* (2013.01); *G06F 3/038* (2013.01); *G06F 3/0482* (2013.01); *G06F 3/0489* (2013.01); *G06F 3/04815* (2013.01); *G06F 3/04845* (2013.01); *G06F 19/321* (2013.01); *G06F 2203/04803* (2013.01)

(58) Field of Classification Search
CPC .................... G06T 2207/10016; G06F 3/017
See application file for complete search history.

(56) References Cited

U.S. PATENT DOCUMENTS

| | | | |
|---|---|---|---|
| 6,392,675 B1* | 5/2002 | Becker | G06F 3/04812 715/856 |
| 6,587,131 B1* | 7/2003 | Nakai | G06F 3/04812 715/857 |
| 8,386,927 B1 | 2/2013 | Franklin et al. | |
| 2004/0024303 A1* | 2/2004 | Banks | A61B 5/055 600/407 |

(Continued)

FOREIGN PATENT DOCUMENTS

| | | |
|---|---|---|
| EP | 2 385 451 A1 | 11/2011 |
| JP | 2003-116838 A | 4/2003 |

(Continued)

OTHER PUBLICATIONS

Communication dated Sep. 6, 2016 issued by the International Searching Authority in counterpart International Application No. PCT/KR2016/005614 (PCT/ISA/220/210/237).

(Continued)

*Primary Examiner* — Claudia Dragoescu
(74) *Attorney, Agent, or Firm* — Sughrue Mion PLLC

(57) ABSTRACT

A medical image displaying apparatus includes: a user interface configured to receive a user input with respect to an object that is movable; a display configured to display the object on a medical image in response to the user input; and a controller configured to move the object and change a velocity of the object based on a property of the object.

15 Claims, 41 Drawing Sheets

(56) References Cited

U.S. PATENT DOCUMENTS

| | | |
|---|---|---|
| 2009/0015550 A1 | 1/2009 | Koski |
| 2009/0037840 A1* | 2/2009 | Chen .................... G06F 3/0481 715/784 |
| 2010/0023857 A1 | 1/2010 | Mahesh et al. |
| 2010/0107099 A1* | 4/2010 | Frazier .................... G06F 3/044 715/765 |
| 2010/0128115 A1 | 5/2010 | Nakano |
| 2010/0256459 A1 | 10/2010 | Miyasa et al. |
| 2011/0209085 A1 | 8/2011 | Doar |
| 2013/0321286 A1 | 12/2013 | Petruzzelli et al. |
| 2014/0143716 A1* | 5/2014 | Buelow .................... G06T 7/10 715/788 |
| 2014/0240233 A1 | 8/2014 | Jeong et al. |

FOREIGN PATENT DOCUMENTS

| | | |
|---|---|---|
| JP | 2007-151645 A | 6/2007 |
| JP | 2010-195 A | 1/2010 |
| JP | 2011-101759 A | 5/2011 |
| WO | 2004/109495 A1 | 12/2004 |

OTHER PUBLICATIONS

Communication dated Sep. 30, 2016 issued by the European Patent Office in counterpart European Patent Application No. 16171732.7.

Communication dated Jul. 17, 2019 issued by the European Patent Office in corresponding European Patent Application No. 16171732.7, 11 pages.

Anand Khanse: "Make the mouse pointer move automatically to the dialog box in Windows 7", Mar. 7, 2011 (Mar. 7, 2011), XP055603973, 5 pages. Retrieved from the Internet: URL:https://www.thewindowsclub.com/automatically-move-themouse-pointer-to-the-dialog-box-in-windows [last retrieved on Jul. 9, 2019].

* cited by examiner

FIG. 11

| PROPERTIES OF MEDICAL IMAGE | DISPLAY PROPERTIES OF MEDICAL IMAGE |
|---|---|
| 2D ROTATION | 0°, 90°, 180°, 270°, 360° |
| 3D ROTATION | 0°, 90°, 180°, 270°, 360° |
| ENLARGE | 0.5, 1, 2.0, 3.0 |
| BRIGHTNESS | 100%, 75%, 50%, 25% |
| CONTRAST | 0.5, 1, 1.5, 2.0 |

| USER CONTENT | SWITCHING SPEED OF MEDICAL IMAGE |
|---|---|
| ANNOTATION | 0.3 |
| MARKER | 0.2 |
| ROI(region of interest) | 0.1 |

METHOD AND APPARATUS FOR DISPLAYING MEDICAL IMAGE

CROSS-REFERENCE TO RELATED APPLICATION

This application claims priority from Korean Patent Application No. 10-2015-0075365, filed on May 28, 2015, in the Korean Intellectual Property Office, the disclosure of which is incorporated herein in its entirety by reference.

BACKGROUND

1. Field

The present disclosure relates to apparatuses and methods of displaying medical images.

2. Description of the Related Art

A magnetic resonance imaging (MRI) apparatus is an apparatus for capturing images of an object by using a magnetic field, and is being used widely to diagnose diseases since the MRI apparatus three-dimensionally shows bones, discs, joints, nerves, ligaments, and heart from a desired direction.

The MRI apparatus may generate medical images based on an MR signal obtained from an object. The medical images may be displayed on the MRI apparatus or an independent display apparatus. The MRI apparatus or the independent display apparatus may provide various graphical user interface (GUI) by which a user may control medical images.

SUMMARY

Additional aspects will be set forth in part in the description which follows and, in part, will be apparent from the description, or may be learned by practice of the exemplary embodiments.

According to an aspect of an exemplary embodiment, a medical image displaying apparatus includes: a user interface configured to receive a user input with respect to an object that is movable; a display configured to display the object on a medical image including at least one GUI in response to the user input; and a controller configured to change a velocity of the object based on properties of the object.

The object may be a cursor moving on a screen in which the medical image is displayed, and the controller may change the velocity of the cursor based on cursor sensitivity information.

The cursor sensitivity information may be determined based on a location of the at least one GUI.

The cursor sensitivity information may be determined based on distances among a plurality of GUIs, if a plurality of GUIs is included in the medical image.

The controller may be configured to generate a new GUI, and to update the cursor sensitivity information based on the location of the at least one GUI and a location of the new GUI.

When there is the at least one GUI within a first critical range from the new GUI, the controller may be configured to increase a sensitivity of the cursor corresponding to the first critical range, and the at least one GUI does not exist within the first critical range from the new GUI, the controller may be configured to decrease the sensitivity of the cursor corresponding to the first critical range.

The user interface may be configured to receive a user input for selecting a property changing GUI for changing properties of the medical image among the at least one GUI, and the controller may be configured to change the property of the medical image to a property value that is determined in advance, based on the user input for selecting the property changing GUI.

The user interface may be configured to receive a user input for inputting a key, and the controller may be configured to select a GUI located on a direction in which the cursor is moving, based on a moving direction of the cursor when the key is input.

According to an aspect of an exemplary embodiment, a medical image displaying apparatus includes: a user interface configured to receive a user input; a display configured to switch a first medical image to a second medical image included in a plurality of medical images, and display the second medical image, based on the user input; and a controller configured to change a switching speed from the first medical image to the second medical image based on whether the first medical image includes user content.

The switching speed may be dependent upon a type of user content included in the first medical image.

The user content may include at least one of an annotation, a marker, and a region of interest (ROI) generated by the user.

According to an aspect of an exemplary embodiment, a medical image displaying method includes: receiving a user input with respect to an object that is movable; displaying the object that is movable on a medical image including at least one GUI, in response to the user input; and changing a velocity of the object based on properties of the object.

The object may be a cursor that moves on a screen in which the medical image is displayed, and the changing of the velocity of the object may include changing the velocity of the cursor based on cursor sensitivity information.

The cursor sensitivity information may be determined based on a location of the at least one GUI.

The cursor sensitivity information may be determined based on distances among a plurality of GUIs, if a plurality of GUIs is included in the medical image.

The medical image displaying method may further include: generating a new GUI; and updating the cursor sensitivity information based on the location of the at least one GUI and a location of the new GUI.

The updating of the cursor sensitivity information may include: when there is the at least one GUI within a first critical range from the new GUI, increasing a sensitivity of the cursor corresponding to the first critical range; and when the at least one GUI does not exist within the first critical range from the new GUI, decreasing the sensitivity of the cursor corresponding to the first critical range.

The medical image displaying method may further include: receiving a user input for selecting a property changing GUI for changing properties of the medical image among the at least one GUI; and changing the property of the medical image to a property value that is determined in advance, based on the user input for selecting the property changing GUI.

The medical image displaying method may further include: receiving a user input for inputting a key; and selecting a GUI located on a direction in which the cursor is moving, based on a moving direction of the cursor when the key is input.

According to an aspect of an exemplary embodiment, a medical image displaying method includes: receiving a user input; switching a first medical image to a second medical image included in a plurality of medical images based on the user input, and displaying the second medical image; and changing a switching speed from the first medical image to the second medical image, based on whether the first medical image includes user content.

The switching speed may be determined based on a type of the user content included in the first medical image.

The user content may include at least one of an annotation, a marker, and an ROI.

BRIEF DESCRIPTION OF THE DRAWINGS

The above and/or other aspects will become more apparent by describing certain exemplary embodiments with reference to the accompanying drawings, in which:

FIG. 11 is a diagram of an example of predetermined property values corresponding to various properties of a medical image;

FIG. 25 is a table of an example of reducing a switching speed according to user content;

DETAILED DESCRIPTION

Figure 1:
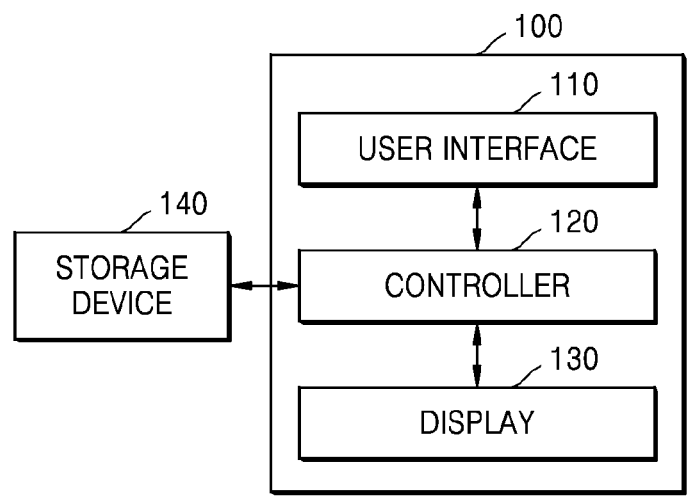
FIG. 1 is a block diagram illustrating an example structure of a medical image displaying apparatus.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The attached drawings for illustrating exemplary embodiments of the present disclosure are referred to in order to gain a sufficient understanding of the present disclosure, the merits thereof, and the objectives accomplished by the implementation of the present disclosure. In this regard, the exemplary embodiments may have different forms and should not be construed as being limited to the descriptions set forth herein. Rather, these embodiments are provided so that this disclosure will be thorough and complete and will fully convey the concept of the exemplary embodiments to one of ordinary skill in the art, and the present disclosure will only be defined by the appended claims.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Throughout the specification, a "medical image" may mean multi-dimensional data formed of discrete image elements, e.g., pixels in a 2D image and voxels in a 3D image. For example, the medical image may be a medical image of an object captured by an X-ray apparatus, a computed tomography (CT) apparatus, an MRI apparatus, an ultrasound diagnostic apparatus, or another medical imaging apparatus.

Furthermore, in the present specification, a "body" may be a human, an animal, or a part of a human or animal. For example, the body may be an organ (e.g., the liver, the heart, the womb, the brain, a breast, or the abdomen), a blood vessel, or a combination thereof. Furthermore, the "body" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of a body obtained by using the nuclear magnetic resonance principle.

An MRI system is an apparatus for acquiring a sectional image of a part of a body by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is emitted for an instant toward the body placed in a strong magnetic field and then such emission stops, an MR signal is emitted from the specific atomic nucleus, and thus the MRI system may receive the MR signal and acquire an MR image. The MR signal denotes an RF signal emitted from the body. An intensity of the MR signal may be determined according to a density of a predetermined atom (for example, hydrogen) of the body, a relaxation time T1, a relaxation time T2, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose patients or medical staff to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are required to precisely capturing abnormal tissues.

FIG. 1 is a block diagram illustrating an example structure of a medical image displaying apparatus 100.

Referring to FIG. 1, the medical image displaying apparatus 100 may be a medical apparatus such as an X-ray apparatus, a CT apparatus, an MRI apparatus, and an ultrasound diagnostic apparatus. As another example, the medical image displaying apparatus 100 may be an apparatus that receives and processes medical images from a medical apparatus.

The medical image displaying apparatus 100 includes a user interface 110, i.e., a user input receiver, a controller 120, and a display 130.

The user interface 110 may denote a hardware configuration through which a user inputs control information for controlling the medical image displaying apparatus 100. For example, the user interface 110 may include a mouse, a keypad, a dome switch, a touch pad (a touch capacitive-type touch pad, a pressure resistive-type touch pad, an infrared beam-sensing-type touch pad, a surface acoustic wave-type touch pad, an integral strain gauge type touch pad, a piezoelectric effect-type touch pad, or the like), a jog wheel, and a jog switch. The user interface 110 may include a touch screen, a touch panel, a microphone, and a keyboard.

The user interface 110 according to an exemplary embodiment may receive a user input about a movable object. For example, the movable object may be a cursor. The cursor may be a visibly movable image (e.g., a pointer image) according to the user input received through the user interface 110. Also, the movable object may denote each of a plurality of medical images. The plurality of medical images may be a set of medical images that are relevant with one another. For example, the plurality of medical images may be a set of medical images obtained from a predetermined volume of a patient.

The user interface 110 may transmit the control information transmitted from the user to the controller 120.

The user interface 110 may include one or more modules for receiving the control information from the user. For example, the user interface 110 may include a motion recognition module, a touch recognition module, and a voice recognition module.

The touch recognition module senses a touch gesture of the user on a touch screen, and transfers information about the touch gesture to the controller 120. The voice recognition module senses voice of the user by using a voice recognition engine, and transfers sensed voice to the controller 120. The motion recognition module senses a motion of the user that becomes an input receiver, and transfers information about the motion of the user that becomes the input receiver to the controller 120.

The controller 120 may control overall operations of the medical image displaying apparatus 100. For example, the controller 120 may control the user interface 110 and the display 130. The controller 120 may include a hardware configuration including at least one processor such as a central processing unit (CPU), a graphical processing unit (GPU), and an application processor (AP).

The controller 120 according to an exemplary embodiment may move the object based on the control information transmitted from the user interface 110. The controller 120 may control the display 130 to display the object that is moving.

The controller 120 may change a velocity of the object based on properties of the object.

The display 130 may display the object according to control of the controller 120. The display 130 may display a GUI. The display 130 may include a cathode ray tube (CRT) display, a liquid crystal display (LCD), a plasma display panel (PDP) display, an organic light-emitting diode (OLED) display, a field emission display (FED), a light-emitting diode (LED) display, a vacuum fluorescent display (VFD), a digital light processing (DLP) display, a flat panel display (FPD), a 3D display, a transparent display, etc.

The display 130 according to an exemplary embodiment may display the object that is moving. For example, the display 130 may display the cursor that moves according to the user input, or switching of a first medical image to a second medical image according to the user input.

Figure 2:
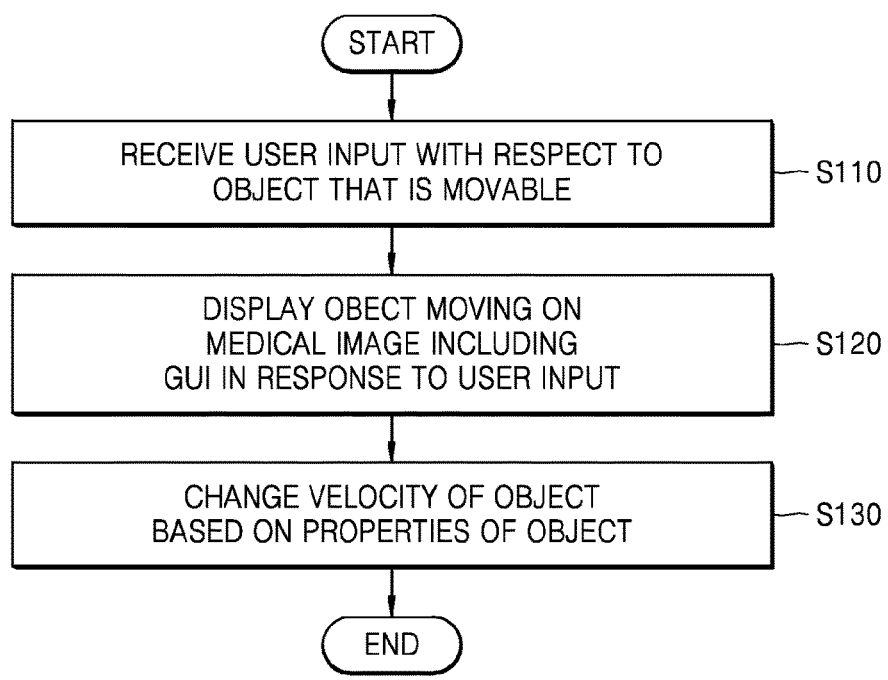
FIG. 2 is a flowchart illustrating an example method of displaying an object in the medical image processing apparatus.

FIG. 2 is a flowchart illustrating an example method of displaying an object by the medical image displaying apparatus 100.

Referring to FIG. 2, the medical image displaying apparatus 100 may receive a user input about an object that is movable (operation S110). For example, the object that is movable may be a cursor that may move within a screen.

The medical image displaying apparatus 100 may display an object that is moving on a medical image including at least one GUI, in response to the user input (operation S120). Also, the medical image displaying apparatus 100 may change a velocity of the object based on properties of the object (operation S130). For example, the medical image displaying apparatus 100 may change the velocity of the cursor based on properties of the cursor.

Figure 3:
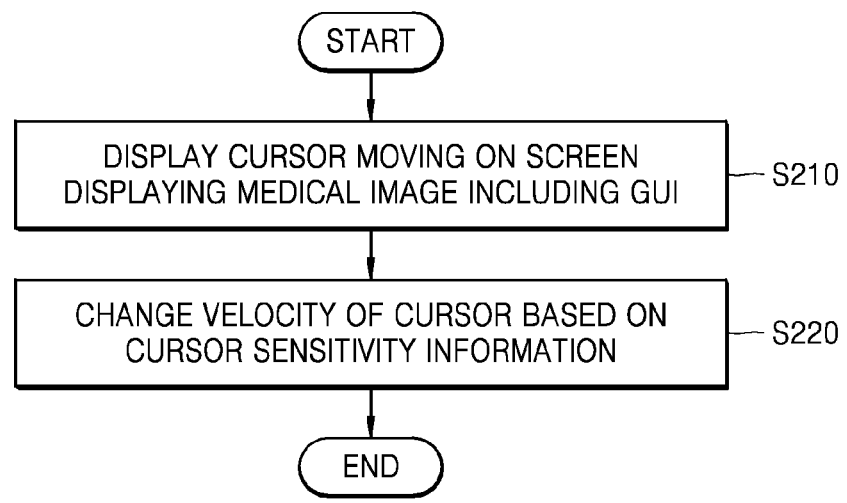
FIG. 3 is a flowchart illustrating an example method, in which the medical image displaying apparatus displays a cursor after actively changing a velocity of the cursor that is moving on a medical image.

As described above, the medical image displaying apparatus 100 changes the velocity of the cursor so that the user may easily manipulate within the medical image. FIG. 3 is a flowchart illustrating an example method of displaying the cursor after actively changing the velocity of the cursor that is moving on the medical image by the medical image displaying apparatus 100.

Referring to FIG. 3, the medical image displaying apparatus 100 may display a cursor that is moving on a screen, on which a medical image including a GUI is displayed (operation S210). For example, the GUI may be a graphical interface item for receiving control information from the user. The medical image displaying apparatus 100 may provide various GUIs within the medical image.

For example, the medical image displaying apparatus may provide at least one among a GUI for setting an ROI in the medical image, a GUI for setting properties of the medical image (e.g., brightness, size, inclination, and rotation of the medical image), and a GUI for selecting a medical image scanning area. The user may control the medical image via the GUI provided in the medical image, by using the cursor.

The medical image displaying apparatus 100 may change the velocity of the cursor based on sensitivity information of the cursor (operation S220). The sensitivity information of the cursor may be information representing movement range of the cursor on the screen in response to the user input for moving the cursor. For example, with respect to the same velocity of the user input, the greater the sensitivity of the cursor is, the less the moving distance of the cursor is, and vice versa. The velocity of the cursor is proportional to a moving distance of the cursor per unit time period, and thus, the medical image displaying apparatus 100 may actively change the velocity of the cursor based on the sensitivity information of the cursor.

The sensitivity information of the cursor may be determined based on location information of the GUI. For example, the medical image displaying apparatus 100 may increase the velocity of the cursor so that the user may easily select the GUI, when the cursor approaches the GUI. As another example, the medical image displaying apparatus 100 may reduce the velocity of the cursor so that the user may manipulate the cursor more accurately, when the cursor is located between two adjacent GUIs. As such, the medical image displaying apparatus 100 may improve user's convenience in manipulating the cursor.

Figure 4A:
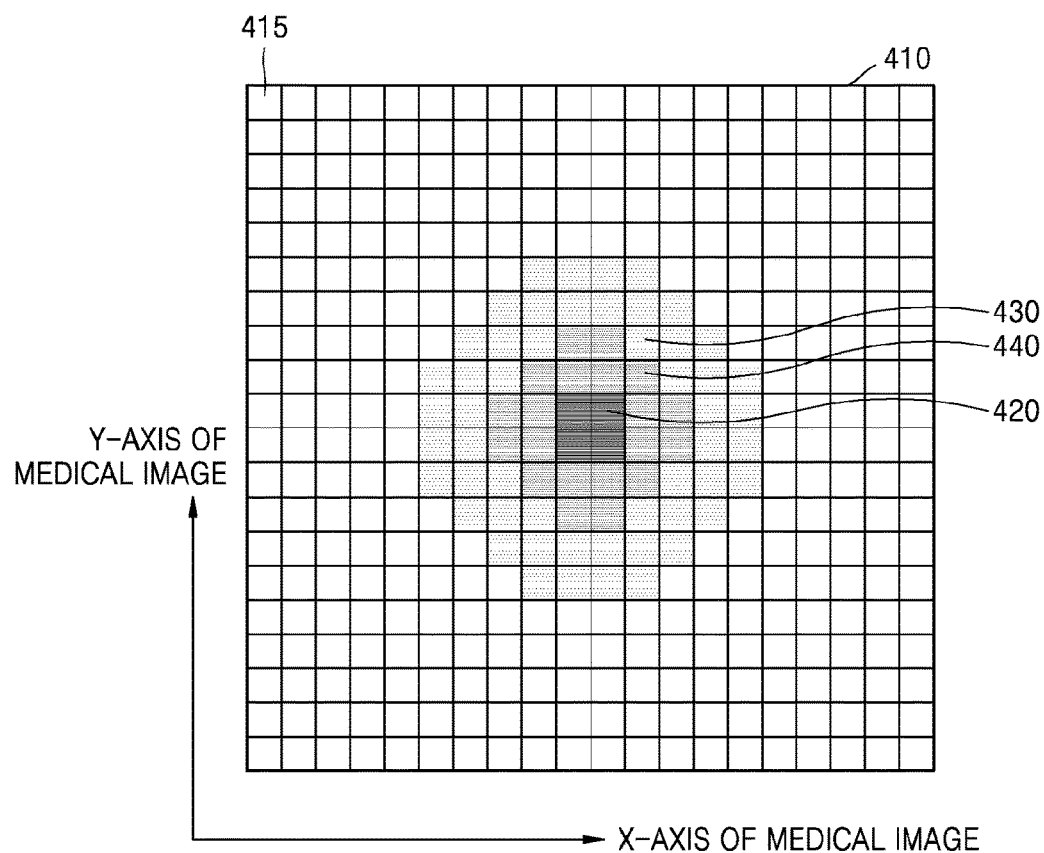
FIG. 4A is a diagram of an example in which a medical image displaying apparatus generates sensitivity information of a cursor based on a location of a GUI.

FIG. 4A is a diagram of an example in which the medical image displaying apparatus 100 generates sensitivity information 410 of the cursor based on a location of the GUI.

Referring to FIG. 4A, the sensitivity information 410 of the cursor may be set as sensitivities of the cursor, which correspond respectively to coordinates 415 on the screen of the medical image displaying apparatus 100. For example, the coordinates 415 each may be location information corresponding to a pixel on the screen of the medical image displaying apparatus 100, or may be location information corresponding to a plurality of pixels. The sensitivity of the cursor may be expressed as a decimal that is greater than 0.0 (e.g., 0.1, 0.2, 0.3, . . . , etc.). For example, the sensitivity information 410 of the cursor may be expressed as a decimal between 0.0 and 2.0.

According to an exemplary embodiment, the controller 120 of the medical image displaying apparatus 100 may generate or update the sensitivity information 410 of the cursor based on the location of a GUI 420 in the medical image.

The controller 120 may generate a sensitivity of the cursor within a first critical range 430 from the location of the GUI 420, to have a value smaller than that of the cursor outside the first critical range 430. For example, if the sensitivity value of the cursor outside the first critical range 430 is 1.0, the sensitivity value of the cursor within the first critical range 430 may be 0.8.

The controller 120 may determine a velocity of the cursor based on a user input speed with respect to the cursor and the sensitivity value of the cursor. For example, when the user input speed with respect to the cursor is 2.0 cm/sec and the sensitivity value of the cursor 1.0, the velocity of the cursor may be 2.0 cm/sec. When the sensitivity value of the cursor 0.8 with respect to the same user input as above, the velocity of the cursor may increase to 2.5 cm/sec. Therefore, the velocity of the cursor within the first critical range 430 may be increased.

Also, the controller 120 may further reduce the sensitivity of the cursor within a second critical range 440 closer to the location of the GUI 420, to be less than the sensitivity of the cursor discussed above with respect to the first critical range 430, for example to 0.4. The sensitivity of the cursor within the second critical range 430 may be a value for moving the cursor to the location of the GUI 420. Therefore, the controller 120 may generate the sensitivity of the cursor that may vary depending on each coordinate within the second critical range 430. Therefore, when the cursor moves into the second critical range 430, the medical image displaying apparatus 100 may increase the velocity of the cursor toward the location of the GUI 420. Accordingly, the user may experience a magnet effect, that is, the user may feel as if the cursor is drawn by the GUI 420 as the cursor is being closer to the GUI 420.

Also, when a new GUI is generated in the medical image, the controller 120 may update the sensitivity information 420 of the cursor based on locations of the existing GUI 420 and the new GUI.

In addition, if a plurality of GUIs is included in the medical image, the controller 120 may generate or update the sensitivity information 410 of the cursor based on distances between the plurality of GUIs. The controller 120 may determine whether a first critical range from each of the plurality of GUIs overlaps the others. If the first critical ranges of the plurality of GUIs do not overlap each other, the controller 120 may generate the sensitivity information 410 of the cursor in the above-described manner. A method of generating the sensitivity information 410 of the cursor by the controller 120 when the first critical ranges of the plurality of GUIs overlap one another will be described below with reference to FIG. 5.

In the above description, the sensitivity information of the cursor is described to be differently determined according to the first and second critical ranges, but an exemplary embodiment is not limited thereto. That is, the sensitivity information of the cursor may be determined according to more than two critical ranges or less, e.g., one critical range.

Figure 4B:
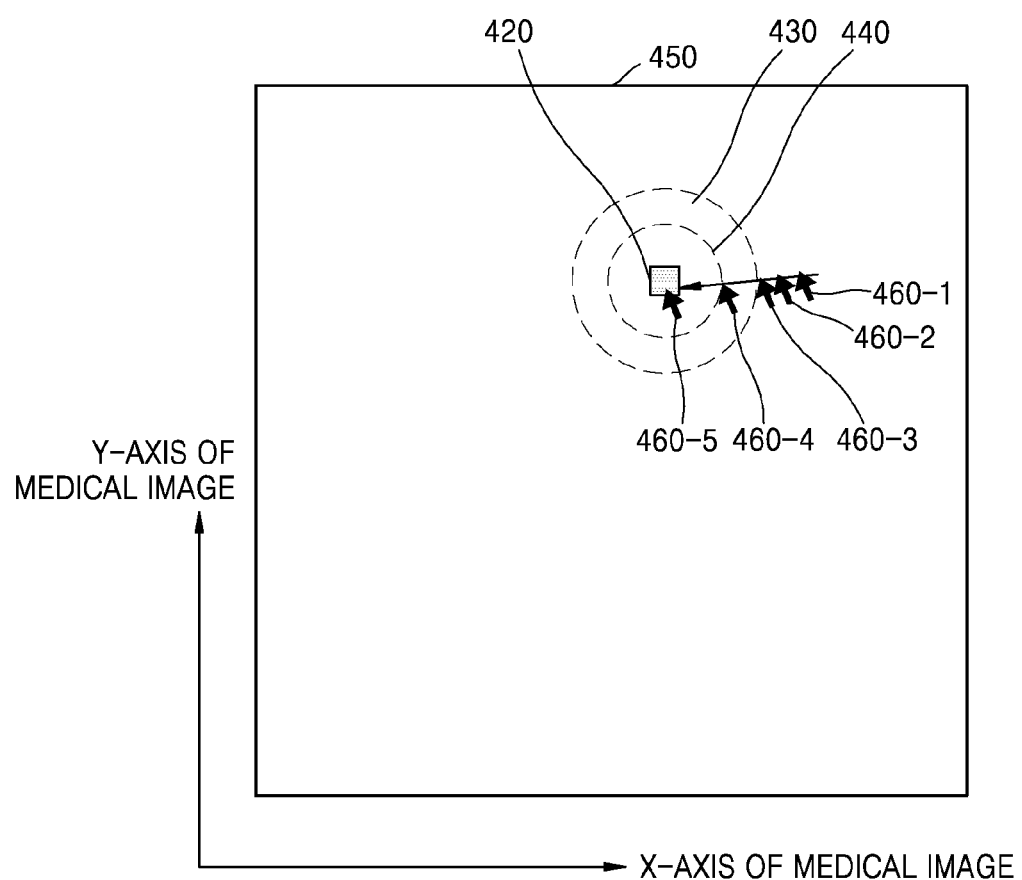
FIG. 4B is a diagram of an example, in which a medical image displaying apparatus makes a cursor approach a GUI.

FIG. 4B is a diagram of an example, in which the medical image displaying apparatus 100 makes the cursor approach the GUI 420. As shown in FIG. 4B, the medical image displaying apparatus 100 may receive user inputs with respect to cursors 460-1, 460-2, 460-3, 460-4, and 460-5, wherein the user inputs velocities are equal to one another. For example, the user interface 110 of the medical image displaying apparatus 100 may receive a user input for moving a mouse toward the GUI 420 at a constant velocity. The medical image displaying apparatus 100 may increase the velocities of the cursors 460-1 to 460-5 based on the sensitivity information 410 of the cursor shown in FIG. 4A. Therefore, the user may easily select the GUI 420 by moving the cursor close to the GUI 420.

Figure 5:
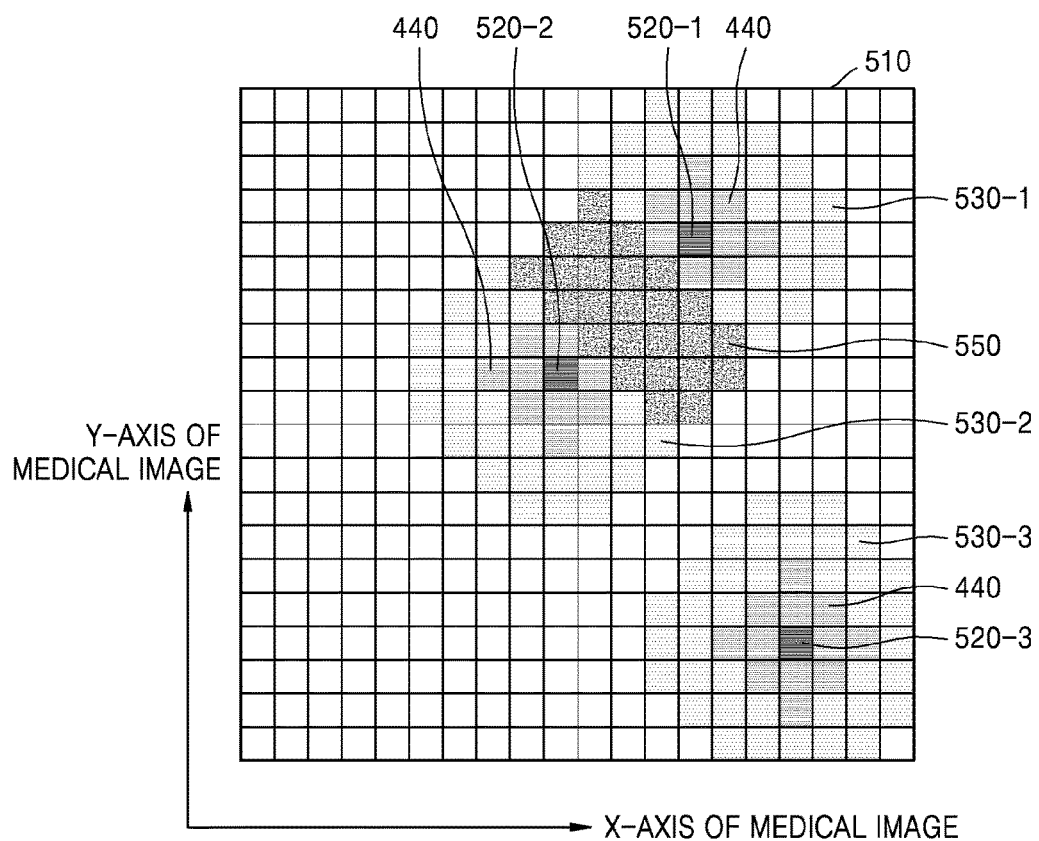
FIG. 5 is a diagram of an example, in which a medical image displaying apparatus generates sensitivity information of a cursor based on locations among a plurality of GUIs.

FIG. 5 is a diagram of an example, in which the medical image displaying apparatus 100 generates sensitivity information 510 of the cursor based on locations among the plurality of GUIs.

Referring to FIG. 5, the controller 120 of the medical image displaying apparatus 100 may determine the sensitivity information 510 of the cursor based on distances between the plurality of GUIs 520-1 to 520-3. For example, when a first critical range 530-1 of the first GUI 520-1 and a first critical range 530-2 of the second GUI 520-2 overlap each other in a region 550, the controller 120 may increase a sensitivity of a cursor corresponding to a region between the first GUI 520-1 and the second GUI 520-2 (hereinafter, referred to as a "crowded region 550"). For example, the controller 120 may set the sensitivity of the cursor within the crowded region 550 as 1.2.

The controller 120 may determine the velocity of the cursor based on a user input speed with respect to the cursor and the sensitivity value of the cursor. For example, when the user input speed with respect to the cursor is 2.0 cm/sec and the sensitivity value of the cursor is 1.0, the velocity of the cursor may be 2.0 cm/sec. When the sensitivity of the cursor is 1.2 with respect to the same user input, the velocity of the cursor may be reduced to 1.6 cm/sec. As described above, if the same user input for moving the cursor is received, the controller 120 may reduce the velocity of the cursor within the crowded region 550.

The controller 120 may reduce second critical ranges 540-1 and 540-2 of the first and second GUIs 520-1 and 520-2, in order to prevent the cursor from moving toward an undesired GUI due to the magnet effect.

Also, the controller 120 may reduce the sensitivity of the cursor within the first critical ranges 530-1 and 530-2 of the first and second GUIs 520-1 and 520-2, except for the crowded region 550. In addition, since the third GUI 520-3 is farther away from the first and second GUIs 520-1 and 520-2, the controller 120 may reduce the sensitivity of the cursor within a first critical range 530-3 of the third GUI 520-3.

Figure 6:
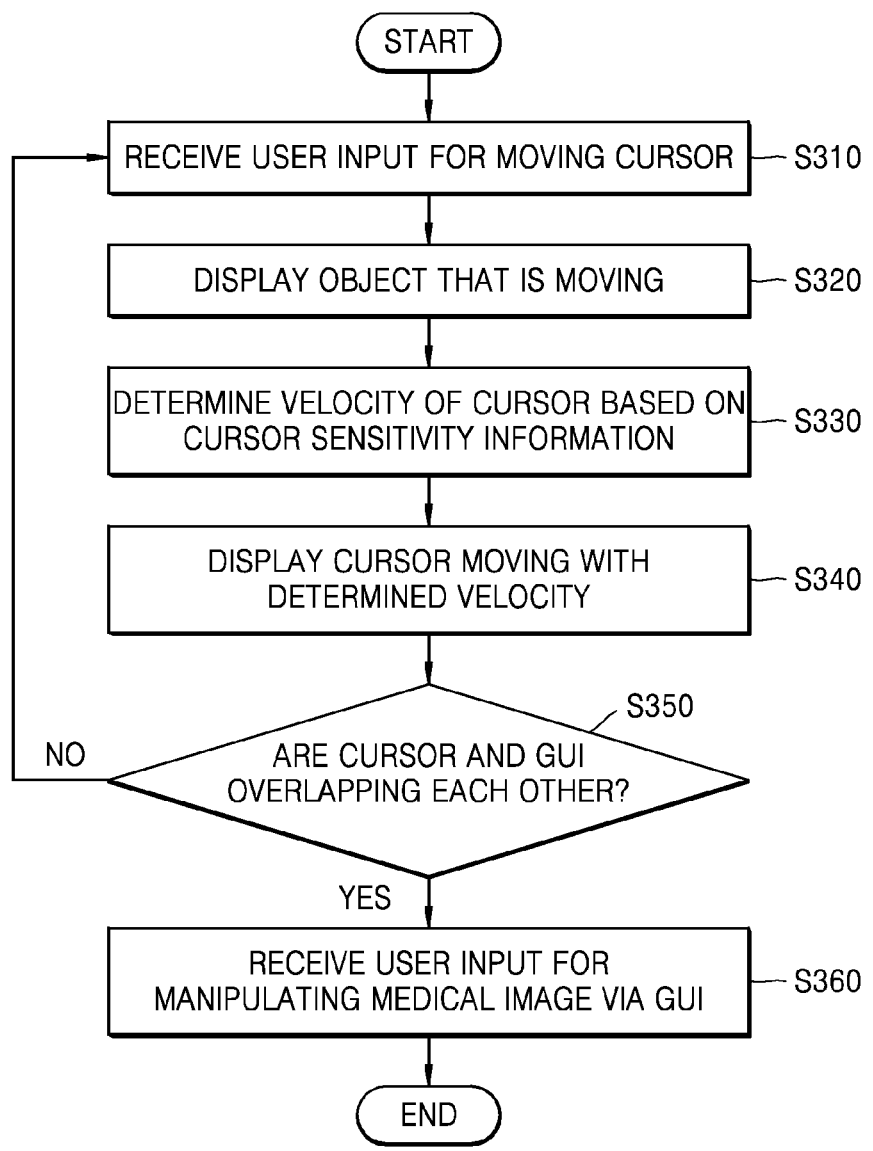
FIG. 6 is a flowchart illustrating an example method in which a medical image displaying apparatus manipulates a medical image via a GUI.

FIG. 6 is a flowchart illustrating an example method in which the medical image displaying apparatus 100 manipulates the medical image via the GUI.

Referring to FIG. 6, the medical image displaying apparatus 100 may receive a user input for moving the cursor (operation S310). The medical image displaying apparatus 100 calculates a location of the cursor that is moved according to the user input, and obtains the sensitivity information of the cursor corresponding to the calculated location of the cursor (operation S320). Also, the medical image displaying apparatus 100 may determine the velocity of the cursor based on the sensitivity information of the cursor (operation S330). For example, if the sensitivity information of the cursor is less than 1.0, the velocity of the cursor may increase. As another example, if the sensitivity information of the cursor is greater than 1.0, the velocity of the cursor may be reduced.

The medical image displaying apparatus 100 may display the cursor that is moving with the determined velocity (operation S340). For example, when the medical image displaying apparatus 100 receives a user input for moving the cursor into the second critical range surrounding the location of the GUI, the cursor may be automatically moved to the location of the GUI.

The medical image displaying apparatus 100 may determine whether the cursor and the GUI are displayed as overlapping each other (operation S350). If the cursor overlaps the GUI, the medical image displaying apparatus 100 may display a mark for notifying the user that the medical image may be manipulated via the GUI. For example, the medical image displaying apparatus 100 may change a color of the GUI or a size of the GUI.

The medical image displaying apparatus 100 may receive a user input for manipulating the medical image via the GUI (operation S360). For example, the medical image displaying apparatus 100 may receive a user input for setting an ROI via the GUI for setting the ROI. As another example, the medical image displaying apparatus 100 may receive a user input for changing properties of the medical image via the GUI for changing the properties of the medical image.

If the cursor and the GUI do not overlap each other, the medical image displaying apparatus 100 may receive a user input for moving the cursor again (operation S310).

Figure 7:
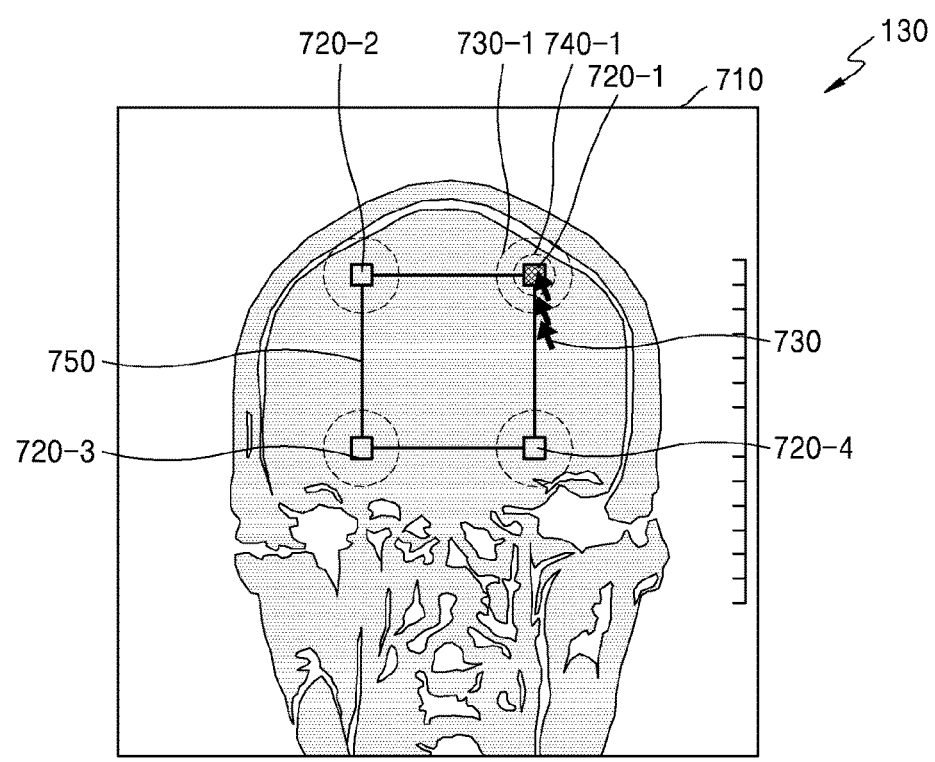
FIG. 7 is a diagram showing an example, in which a medical image displaying apparatus sets an ROI on a medical image via a GUI.

FIG. 7 is a diagram showing an example, in which the medical image displaying apparatus 100 sets an ROI 750 on the medical image via the GUI.

Referring to FIG. 7, the display 130 of the medical image displaying apparatus 100 may display a medical image 710 including first to fourth ROI setting GUIs 720-1, 720-2, 720-3, and 720-4 for setting an ROI. The display 130 may display a cursor 730 that moves according to a user input.

When the cursor 730 is located within a first critical range 730-1 of the first ROI setting GUI 720-1, the controller 120 of the medical image displaying apparatus 100 may increase a velocity of the cursor 730. When the cursor 730 is located within a second critical range 740-1 of the first ROI setting GUI 720-1, the controller 120 may move the cursor 730 to a location of the first ROI setting GUI 720-1.

Also, the user interface 110 of the medical image displaying apparatus 100 may receive a user input for moving the first ROI setting GUI 720-1 in a state where the cursor 730 and the first ROI setting GUI 720-1 overlap each other. The controller 120 of the medical image displaying apparatus 100 may set the ROI based on the user input.

Figure 8:
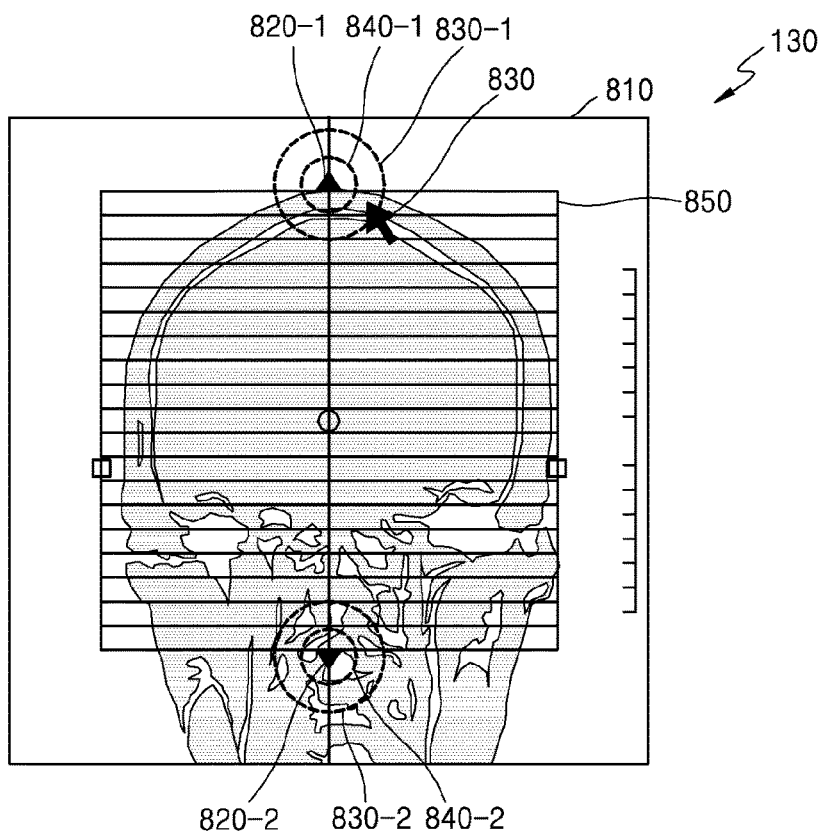
FIG. 8 is a diagram of an example, in which a medical image displaying apparatus sets a medical image scanning region via a GUI.

FIG. 8 is a diagram of an example, in which the medical image displaying apparatus 100 sets a medical image scanning region via the GUI.

Referring to FIG. 8, the display 130 of the medical image displaying apparatus 100 may display a medical image 810 including volume selection GUIs 820-1 and 820-2 for setting a medical image scanning region 850. Also, the display 130 may display a cursor 830 that is moving.

The controller 120 of the medical image displaying apparatus 100 may increase a velocity of the cursor 830, when the cursor 830 approaches the volume selection GUIs 820-1 and 820-2.

The controller 120 may determine a sensitivity of the cursor 830 according to a degree of separation between the GUIs in the medical image. For example, the controller 120 may set the first critical ranges 830-1 and 830-2 and second critical ranges 840-1 and 840-2 of the volume selection GUIs 820-1 and 820-1 shown in FIG. 8 to be of a greater size than the first and second critical ranges of the ROI setting GUIs 720-1 to 720-4 shown in FIG. 7. The controller 120 may subdivide the critical range by which the sensitivity information of the cursor is divided, according to the separation degree between the GUIs in the medical image 810.

Figure 9:
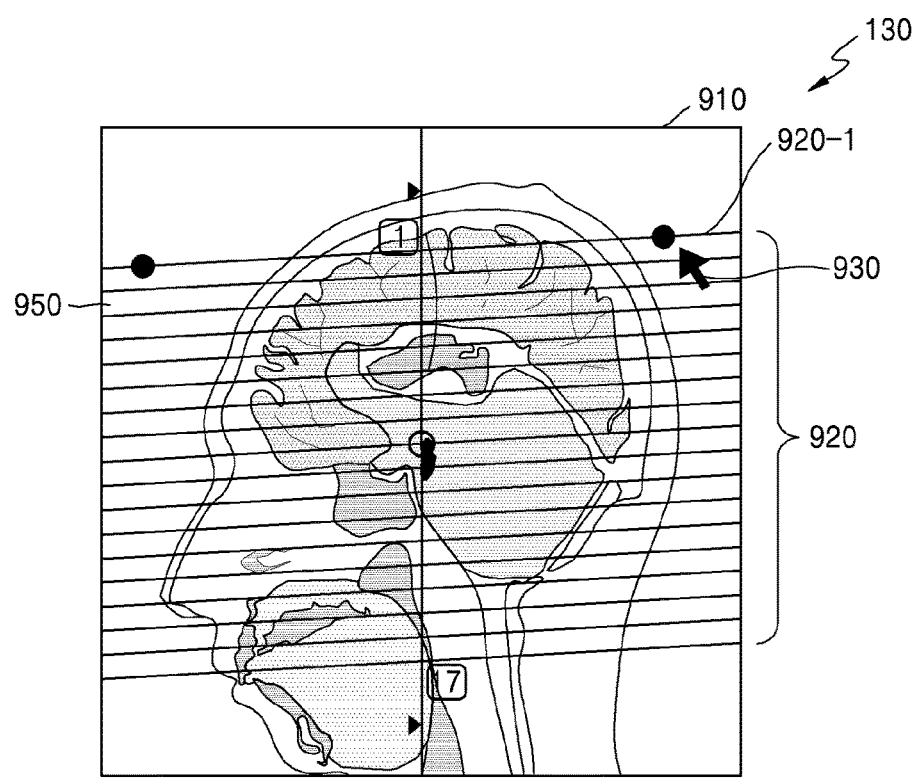
FIG. 9 is a diagram of another example, in which a medical image displaying apparatus sets a medical image scanning region via a GUI.

FIG. 9 is a diagram of another example, in which the medical image displaying apparatus 100 sets slices 950 of a medical image scanning region via the GUI.

Referring to FIG. 9, the display 130 of the medical image displaying apparatus 100 may display a medical image 910 including a plurality of slice selection GUIs 920 for selecting a medical image scanning region. The slice selection GUI 920 may be provided as slice lines selection GUIs 920-1 in the medical image 910, and the slice lines selection GUIs 920-1 may be adjacent to each other in the medical image. Therefore, it may be difficult for the user to select and adjust a desired slice by using a cursor 930.

According to an exemplary embodiment, the controller 120 of the medical image displaying apparatus 100 may reduce a velocity of the cursor 930 moving between the slice lines selection GUIs 920-1 that are adjacent to one another. Accordingly, the cursor 930 may finely move within between the slice selection GUI 920. Therefore, the user may finely adjust the slice lines selection GUIs 920-1 that are adjacent to one another.

Figure 10:
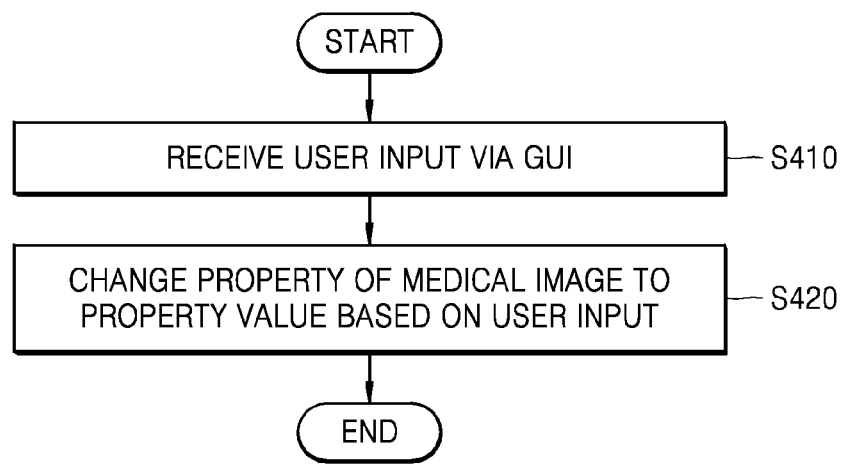
FIG. 10 is a flowchart illustrating an example method in which a medical image displaying apparatus changes properties of a medical image via a GUI.

FIG. 10 is a flowchart illustrating an example method in which the medical image displaying apparatus 100 may change properties of a medical image via a GUI.

Referring to FIG. 10, the medical image displaying apparatus 100 may receive a user input with respect to the GUI (operation S410). For example, the medical image displaying apparatus 100 may receive a user input for pushing a button on a mouse, in a state where the cursor and the GUI overlap each other. Also, the medical image displaying apparatus 100 may receive a user input for moving the GUI (e.g., the slice selection GUI, a medical image rotation GUI, etc.) in a state where the pushed state of the button maintains. As another example, the medical image displaying apparatus 100 may provide a shortcut key or a function key (e.g., a rotation key for rotating the medical image) with respect to the GUI.

According to an exemplary embodiment, the medical image displaying apparatus 100 may change a property of the medical image to a property value that is determined in advance, based on the user input with respect to the GUI (operation S430). The property value determined in advance may include property values corresponding to various properties of the medical image (e.g., 2D or 3D rotation, enlarging, brightness and/or contrast adjustment, etc.).

The medical image displaying apparatus 100 may determine the property values corresponding to the properties, based on a utilization frequency of the user.

As another example, the medical image displaying apparatus 100 may determine the property values corresponding to the properties, based on a characteristic of the medical image (e.g., a brain image, a knee image, etc.). As another example, the property values determined in advance may be input by the user.

The medical image displaying apparatus 100 may receive, for example, a user input with respect to an image enlarging GUI for enlarging the medical image. The medical image displaying apparatus 100 may enlarge the medical image according to the property value that is determined in advance. Therefore, the user may select desired property value by inputting a user input with respect to the property GUI, without inputting the property values corresponding to the properties of the medical image.

FIG. 11 is a diagram of an example of the predetermined property values corresponding to various properties of the medical image; however, this is only a non-limiting example. For example, the predetermined property values may be stored as a table 138 in a storage device 140 (refer to FIG. 1).

Referring to FIG. 11, the property values corresponding to the 2D or 3D rotation property of the medical image may include 0°, 90°, 180°, and 270°. For example, the rotation property values that are determined in advance may denote a degree of rotating the medical image based on an initial medical image. If the initial medical image is a 2D image, the medical image displaying apparatus 100 may change the 2D rotation property. As another example, if the initial medical image is a 3D image, the medical image displaying apparatus 100 may change the 3D rotation property.

The enlarging property values that are determined in advance corresponding to the enlarging property of the medical image may include 0.5, 1.0, 2.0, and 3.0. For example, the enlarging property values may denote magnitudes of enlarging the medical image based on the initial medical image. For example, when the enlarging property value is 2.0, the medical image displaying apparatus 100 may increase transverse and longitudinal lengths to be longer than those of the initial medical image by a factor of 2.

The brightness property values that are determined in advance corresponding to the brightness property of the medical image may include 0%, 25%, 50%, 75%, and 100%. For example, if the brightness property value is 50%, the medical image displaying apparatus 100 may display the medical image at a brightness level corresponding to half the brightness of the initial medical image. If the brightness property value is 100%, the medical image displaying apparatus 100 may display the medical image at the brightness level of the initial medical image. Likewise, the contrast values may be set as 0.5, 1, 1.5, and 2.0.

The medical image displaying apparatus 100 may change the property of the medical image to one of the property values determined in advance, when the user input with respect to the GUI corresponding to each of the properties is received.

Figure 12:
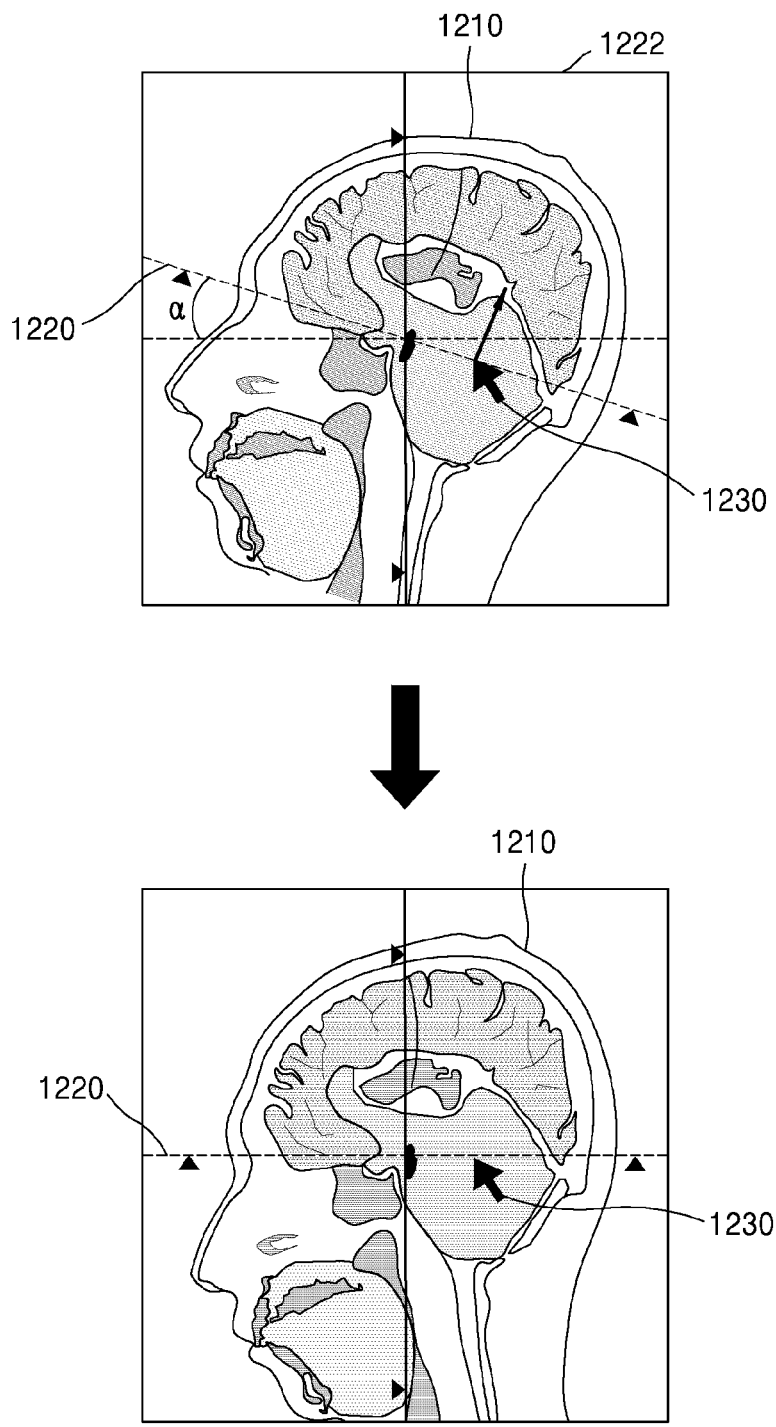
FIG. 12 is a diagram of an example, in which a medical image displaying apparatus rotates a two-dimensional (2D) medical image based on a 2D rotation property value that is determined in advance.

FIG. 12 is a diagram of an example, in which the medical image displaying apparatus 100 rotates a 2D medical image based on a 2D rotation property value that is determined in advance.

Referring to FIG. 12, the controller 120 of the medical image displaying apparatus 100 may provide a 2D rotation GUI 1220 for rotating a 2D medical image 1210 on a screen 1222. For example, the 2D rotation GUI 1220 may be manipulated by using a cursor 1230. When a moving cursor 1230 becomes close to the 2D rotation GUI 1220, the velocity of the moving cursor 1230 may increase.

The medical image displaying apparatus 100 may receive a user input for selecting the 2D rotation GUI 1220. For example, when the medical image displaying apparatus 100 receives the user input for moving a cursor while the user pushes a button of the mouse, the 2D rotation GUI 1220 and the cursor 1230 may be moved together on the screen. For example, the controller 120 may rotate the medical image to a rotation value (e.g.,) 0° that is determined in advance, based on a direction in which the 2D rotation GUI 1220 and the cursor 1230 move.

Since the rotation value 0° that is determined in advance is based on the initial medical image, the display 130 of the medical image displaying apparatus 100 may display the 2D medical image 1210 by rotating the 2D medical image 1210 by about α=10° in a counter-clockwise direction.

Figure 13:
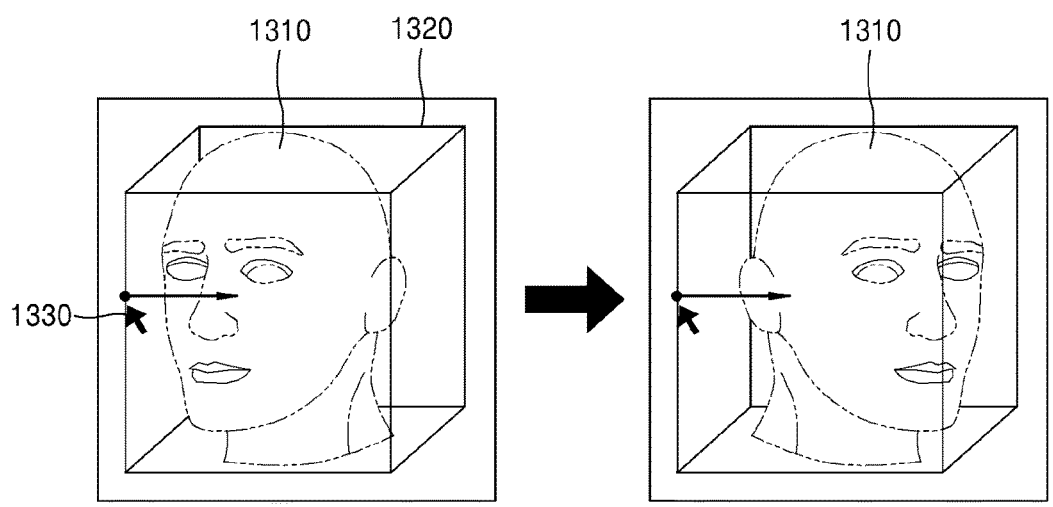
FIG. 13 is a diagram of an example, in which a medical image displaying apparatus rotates a three-dimensional (3D) medical image based on a 3D rotation property value that is determined in advance.

FIG. 13 is a diagram of an example, in which the medical image displaying apparatus 100 rotates a 3D medical image based on a 3D rotation property value that is determined in advance.

Referring to FIG. 13, the controller 120 of the medical image displaying apparatus 100 may provide a 3D rotation GUI 1320 for rotating a 3D medical image 1310. The medical image displaying apparatus 100 may receive a user input with respect to a cursor 1330 for selecting and moving the 3D rotation GUI 1320. For example, the controller 120 may rotate the 3D medical image 1310 by the rotation value (e.g., 90°) that is determined in advance corresponding to the 3D rotation property, based on a direction in which the 3D rotation GUI 1320 moves.

Figure 14:
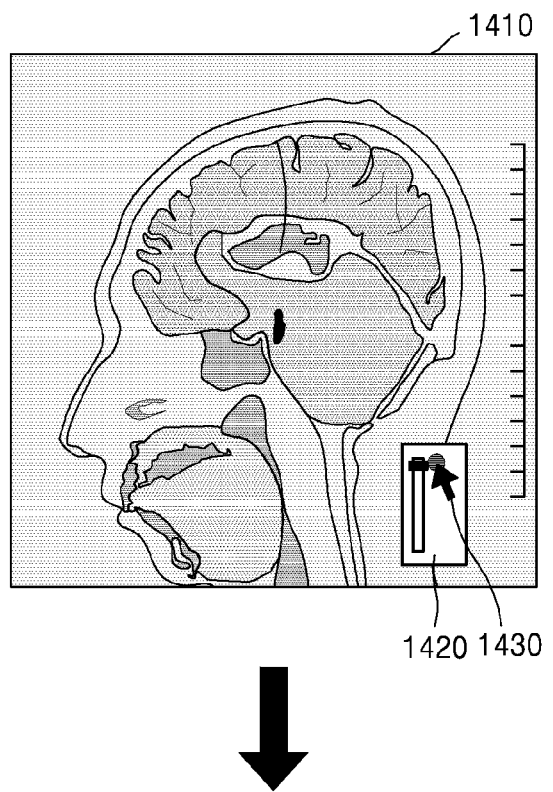
FIG. 14 is a diagram of an example, in which a medical image displaying apparatus changes brightness of a medical image based on an image brightness property that is determined in advance.
Figure 14:
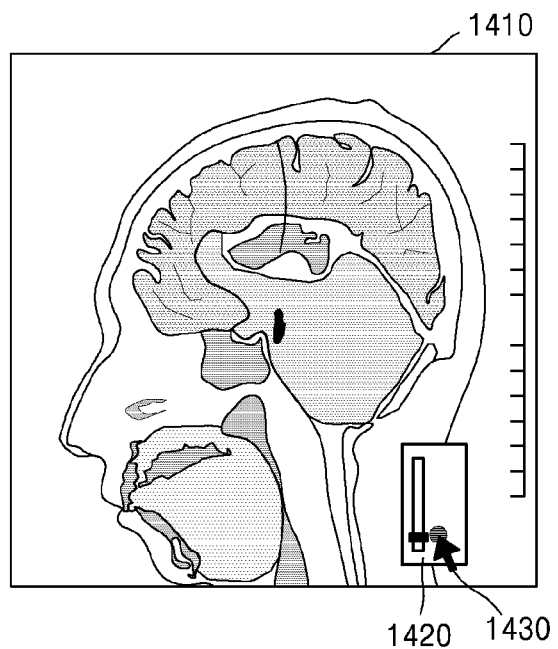

FIG. 14 is a diagram of an example, in which the medical image displaying apparatus 100 changes brightness of the medical image based on the image brightness property that is determined in advance.

Referring to FIG. 14, the controller 120 of the medical image displaying apparatus 100 may provide a brightness property GUI 1420 for changing brightness of a medical image 1410. The controller 120 of the medical image displaying apparatus 100 may change the brightness level of the medical image from 0% to 100%, when receiving a user input 1430 about the brightness property GUI 1420.

Figure 15:
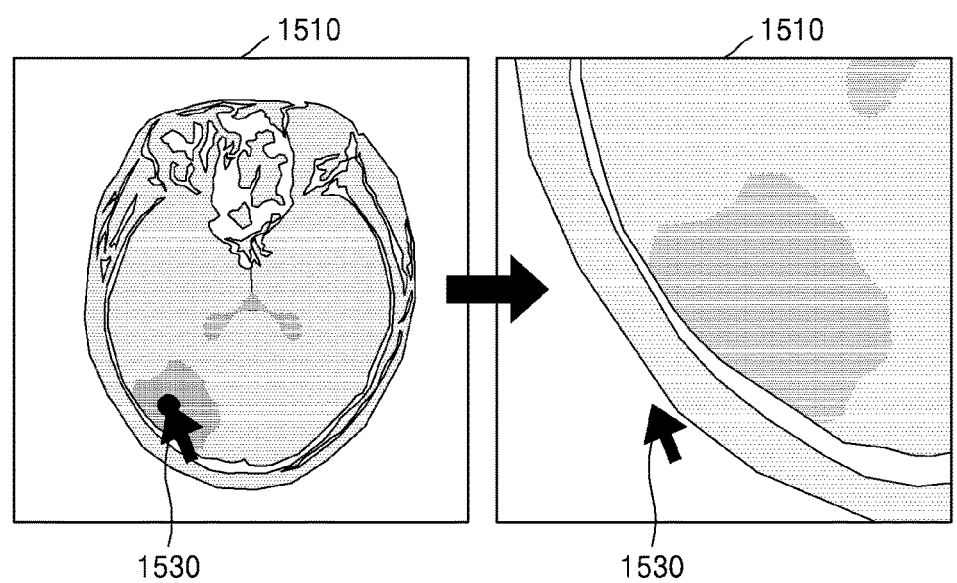
FIG. 15 is a diagram of an example, in which a medical image displaying apparatus enlarges a medical image based on an enlarging property value that is determined in advance.

FIG. 15 is a diagram of an example, in which the medical image displaying apparatus 100 enlarges the medical image based on an enlarging property value that is determined in advance.

Referring to FIG. 15, the user interface 110 of the medical image displaying apparatus 100 may receive a user input 1530 for enlarging a medical image 1510. For example, the user interface 110 may receive a user input that pushes a button of a mouse for a long time period within the medical image 1510. As another example, the user interface 110 may receive a user input that clicks the button of the mouse twice within the medical image 1510.

The controller 120 of the medical image displaying apparatus 100 may double longitudinal and transverse lengths of the medical image 1510, based on the location where the user input 1530 is input, e.g., to increase a specific portion of an image.

Figure 16:
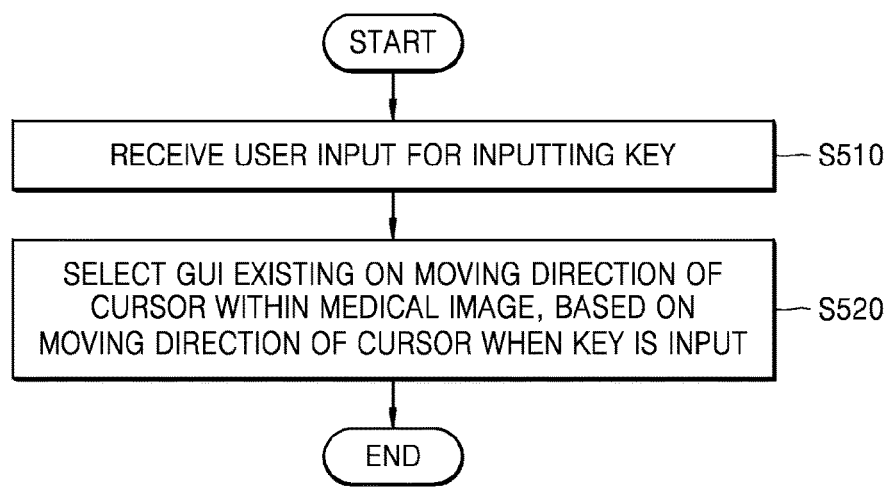
FIG. 16 is a flowchart illustrating a method, in which a medical image displaying apparatus according to an exemplary embodiment selects at least one GUI through a key input.

FIG. 16 is a flowchart illustrating a method, in which the medical image displaying apparatus 100 selects at least one GUI through a key input, according to an exemplary embodiment.

Referring to FIG. 16, the medical image displaying apparatus 100 may receive a user input that pushes a key, during moving a cursor (operation S510). For example, the medical image displaying apparatus 100 may receive a key input that pushes a shortcut key set in advance (e.g., a Ctrl key, a tab key, etc.) or a button of a mouse.

The medical image displaying apparatus 100 may select a GUI that exists in a direction in which the cursor is moving within the medical image, based on the moving direction of the cursor when the key input is received (operation S520). For example, the medical image displaying apparatus 100 may receive a key input while the cursor is moving to a right side. For example, the medical image displaying apparatus 100 may select all GUIs that exist on a right side of the cursor within the medical image. As another example, the medical image displaying apparatus 100 may select a GUI that is adjacent to the cursor among the GUIs that exist on the right side of the cursor within the medical image. The medical image displaying apparatus 100 receives a key input once more so as to select another GUI that is second closest to the cursor next to the selected GUI. The medical image displaying apparatus 100 may move the cursor to the location of the selected GUI whenever a key input is received.

The medical image displaying apparatus 100 may select all the GUIs existing on the moving direction of the cursor or only one GUI by differentiating the type of key that is input. As such, the user does not need to move the cursor to the desired GUI, but may easily select a plurality of GUIs or one GUI by using the key.

Figure 17:
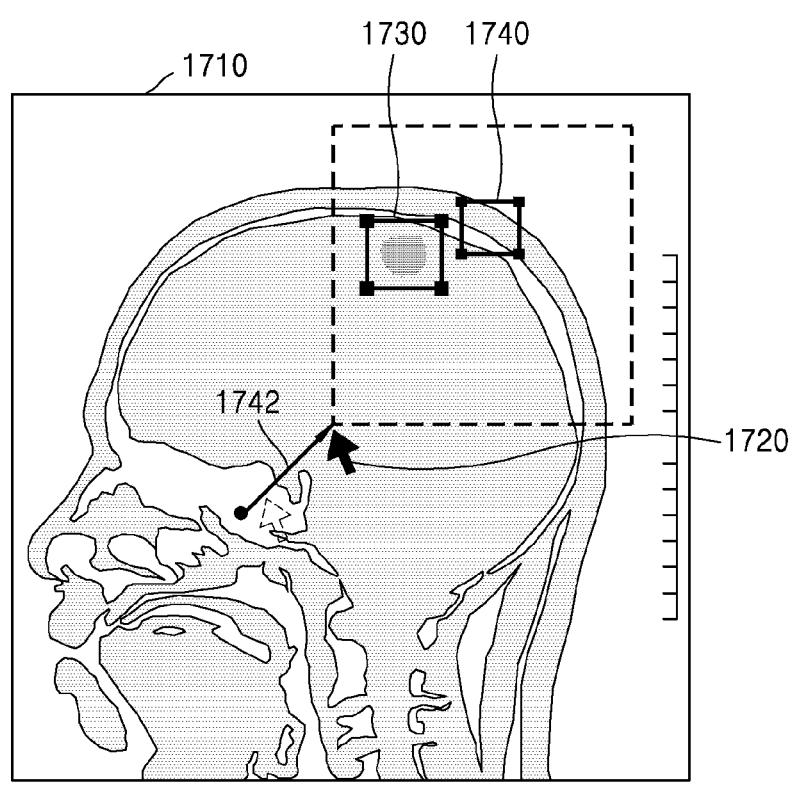
FIG. 17 is a diagram of an example, in which a medical image displaying apparatus selects a plurality of GUIs through a key input.

FIG. 17 is a diagram of an example, in which the medical image displaying apparatus 100 selects a plurality of GUIs through the key input.

As shown in FIG. 17, the controller 120 of the medical image displaying apparatus 100 may select all GUIs 1730 and 1740 existing on a moving direction 1742 of a cursor 1720 within a medical image 1710, based on the moving direction of the cursor 1720 when a key is input.

Figure 18:
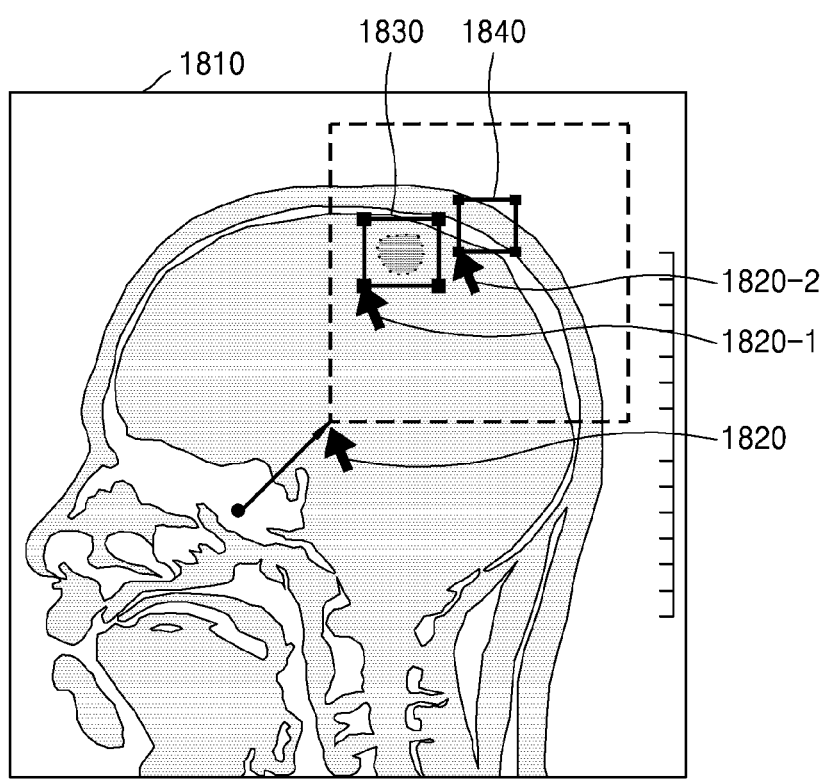
FIG. 18 is a diagram of an example, in which a medical image displaying apparatus selects one GUI through a key input.

FIG. 18 is a diagram of an example, in which the medical image displaying apparatus 100 selects one GUI through the key input. As shown in FIG. 18, the medical image displaying apparatus 100 may select a first ROI setting GUI 1830 that is adjacent to a cursor 1720, among first and second ROI setting GUIs 1830 and 1840 existing on the moving direction of the cursor 1820, based on the moving direction of the cursor 1820 when the key is input. Also, the medical image displaying apparatus 100 may move a cursor to a location 1820-1 of the first ROI setting GUI 1830.

When a key is input once more, the medical image displaying apparatus 100 may select the second ROI setting GUI 1840. Also, the medical image displaying apparatus 100 may move a cursor to a location 1820-2 of the second ROI setting GUI 1840.

Figure 19:
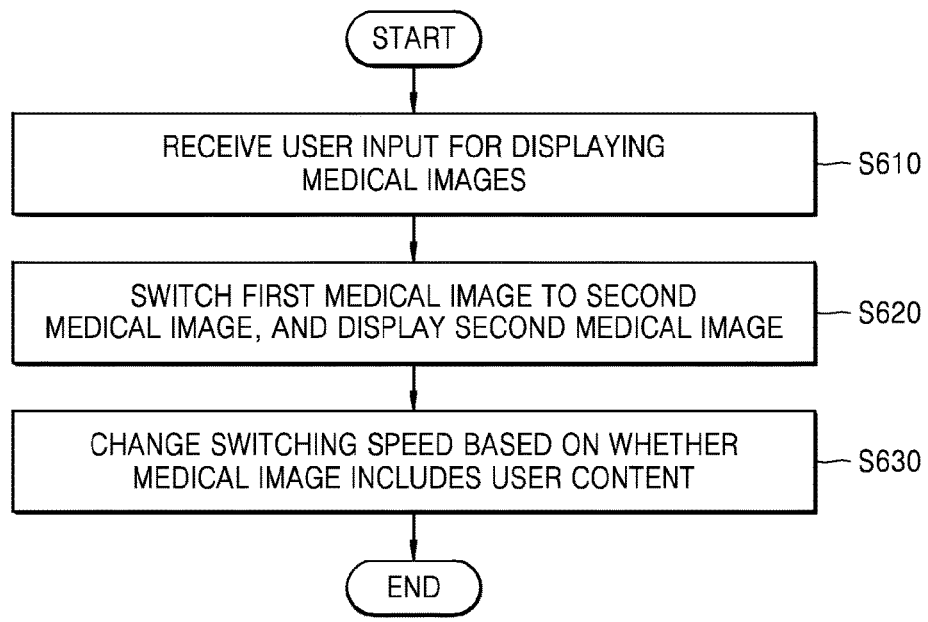
FIG. 19 is a flowchart illustrating an example method in which a medical image displaying apparatus according to an exemplary embodiment displays each of a plurality of medical images.

FIG. 19 is a flowchart illustrating an example method in which the medical image displaying apparatus 100 displays each of a plurality of medical images.

Referring to FIG. 19, the medical image displaying apparatus 100 according to an exemplary embodiment may receive a user input for displaying medical images included in a plurality of medical images (operation S610). For example, the plurality of medical images may be relevant to each other. For example, the plurality of medical images may be a set of slice images obtained from a predetermined volume of a body. As another example, the plurality of medical images may be a set of medical images that are defined to be relevant by the user.

According to an exemplary embodiment, the medical image displaying apparatus 100 may receive a user input that scrolls over the medical images included in the plurality of medical images. For example, scrolling over the plurality of medical images may denote displaying a first medical image followed by a second medical image among the plurality of medical images.

As another example, the medical image displaying apparatus 100 may receive a user input for displaying the first medical image and the second medical image sequentially at a constant location on the screen.

On the other hand, the medical image displaying apparatus 100 may provide a GUI for displaying the medical images included in the plurality of medical images, and may receive the user input about the GUI.

According to an exemplary embodiment, the medical image displaying apparatus 100 may switch the first medical image to the second medical image among the plurality of medical images, and display the second medical image (operation S620). In an exemplary embodiment, the medical image displaying apparatus 100 may display the first and second medical images while moving in a predetermined direction in a state where the first and second medical images included in the plurality of medical images are arranged. As another example, the medical image displaying apparatus 100 may display the first medical image among the plurality of medical images, and after that, may display the second medical image and the subsequent medical images sequentially on the location where the first medical image is displayed. The opposite direction of the display order is also contemplated.

The medical image displaying apparatus 100 may change a switching speed of each medical image, based on whether the medical image includes user content (operation S630). For example, the user content may be content generated by the user or content used by the user, e.g., annotations, markers, and ROIs included in the medical image. The switching speed may denote a speed of switching from the first medical image to the second medical image included in the plurality of images. For example, the switching speed may denote a speed of scrolling over the first medical image and the second medical image that are arranged in a row. As another example, the switching speed may be a value obtained by dividing the total number of the plurality of medical images with a time duration from when the first medical image is displayed to a point when the second medical image is displayed on the screen.

When the medical image includes the user content, the medical image displaying apparatus 100 may reduce the switching speed during the period of displaying the medical image, i.e., to display a certain medical image longer.

The medical image displaying apparatus 100 may vary a degree of reducing the switching speed depending on a type of the user content. For example, if the user content included in the medical image is 'annotation', the switching speed may be reduced by 0.7 times. If the user content included in the medical image is 'marker', the switching speed may be reduced by 0.8 times.

Also, the medical image displaying apparatus 100 may display the medical image including the user content prior to the other medical images, among the plurality of medical images.

As described above, the medical image displaying apparatus 100 may actively change the switching speed of displaying the plurality of medical images, so that the user may easily access certain medical images.

Figure 20:
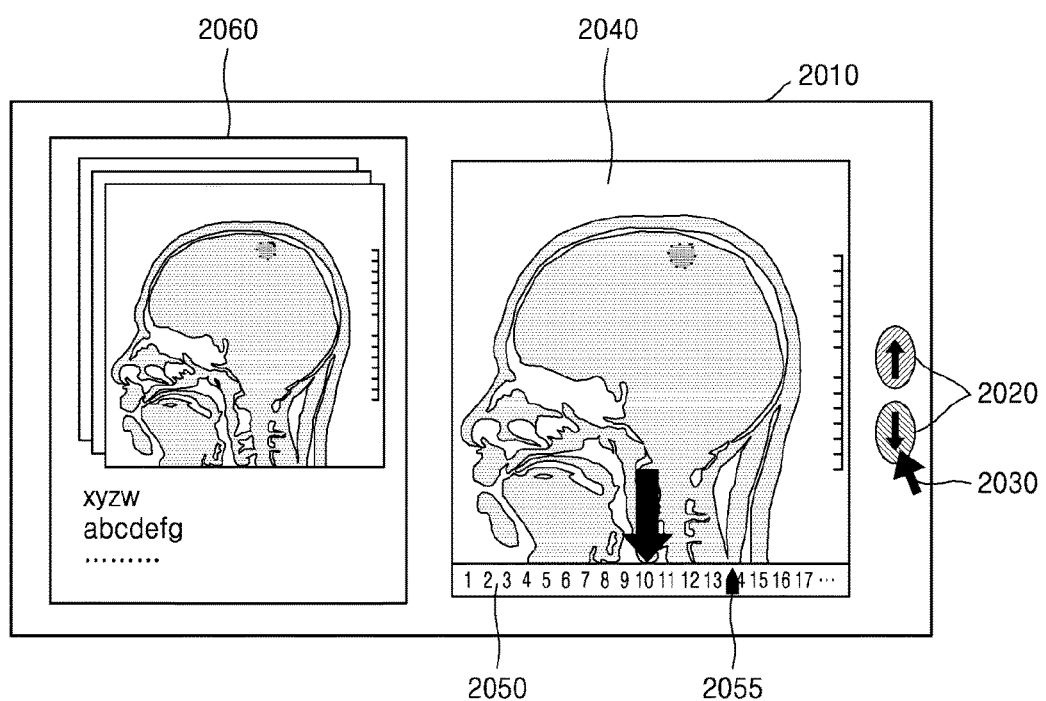
FIGS. 20, 21, and 22 are diagrams showing examples, in which a medical image displaying apparatus displays each medical image while switching a plurality of medical images.
Figure 21:
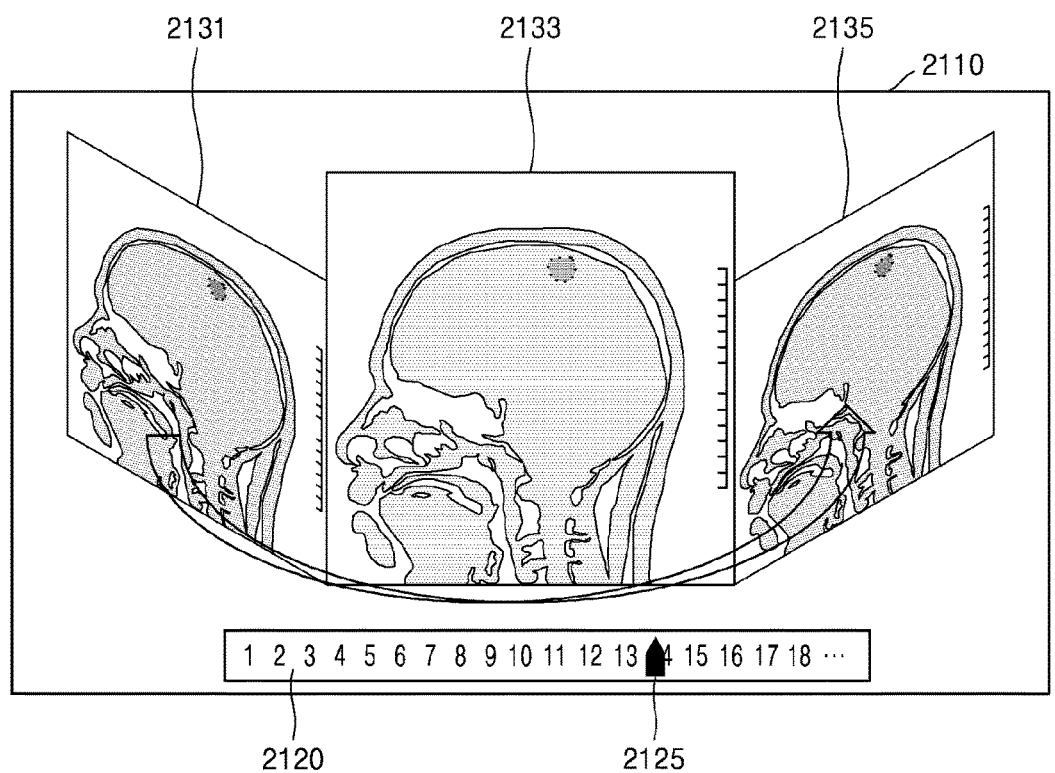
Figure 22:
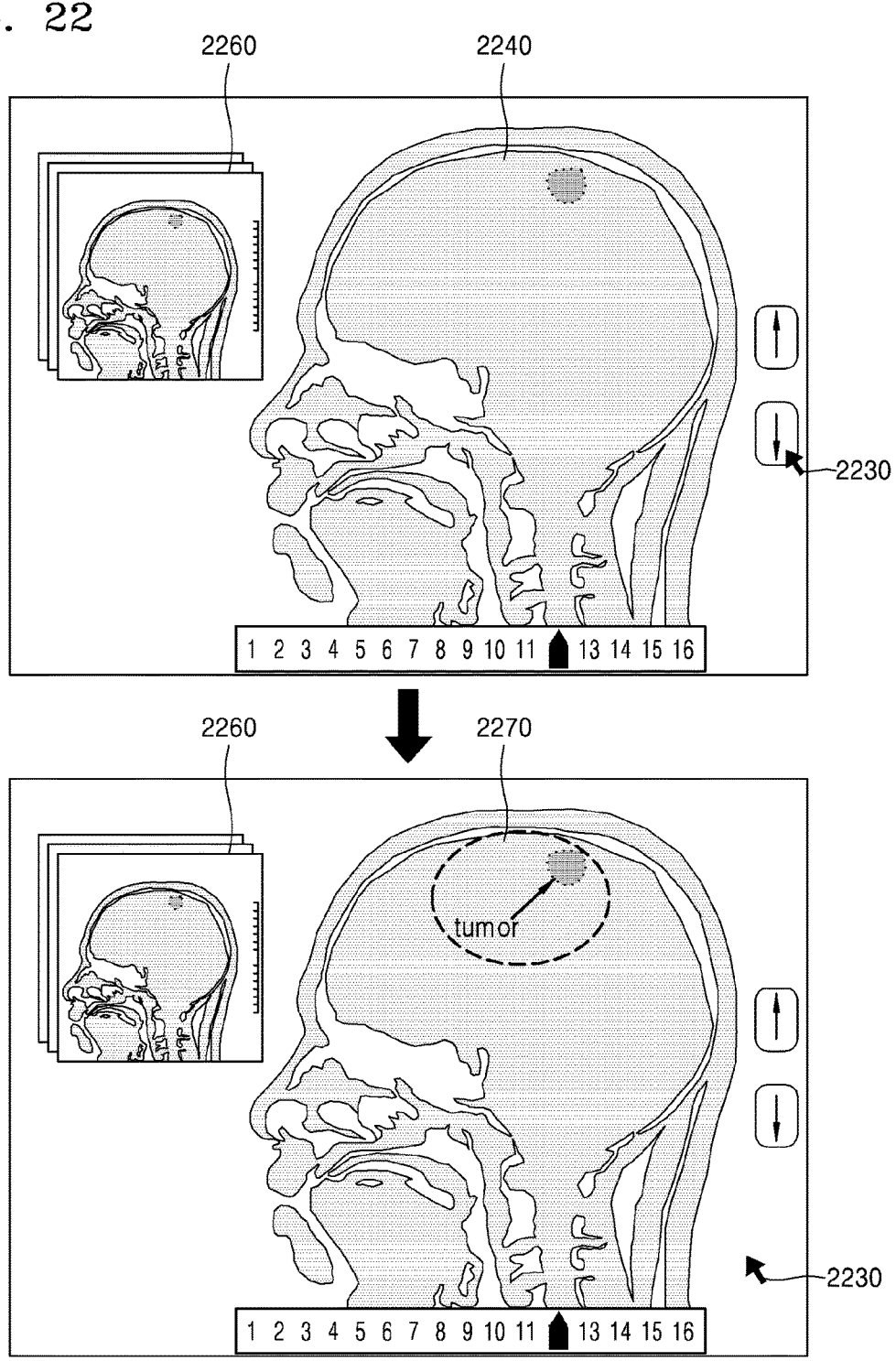

FIGS. 20 to 22 are diagrams showing examples, in which the medical image displaying apparatus 100 displays each medical image while switching the plurality of medical images.

According to an exemplary embodiment, as shown in FIG. 20, the controller 120 of the medical image displaying apparatus 100 displays medical images by scrolling over the screen in a vertical direction in a state where medical images included in a plurality of medical images 2060 are arranged vertically. For example, the medical image displaying apparatus 100 may provide a scroll GUI 2020. When a user input 2030 is received via the scroll GUI 2020, the controller 120 of the medical image displaying apparatus 100 may sequentially display medical images 2040 arranged in a vertical direction.

Also, the display 130 of the medical image displaying apparatus 100 may display an indicator 2055 for indicating a number of medical image that is currently displayed, on a lower end portion 2050 of a screen 2010. For example, the number of medical image may denote a captured order of each of the plurality of medical images. The number of medical images that are displayed on one screen 2010 at the same time may vary depending on a size of the screen 2010 or a size of the medical image.

The medical image displaying apparatus 100 may display information about a medical image 2040 (e.g., time and date of capturing the medical image, and specifics of the patient).

As another example, as shown in FIG. 21, the controller 120 of the medical image displaying apparatus 100 may display each medical image by scrolling over the screen horizontally in a state where a plurality of medical images 2060 are arranged in a horizontal direction. The display 130 of the medical image displaying apparatus 100 may display the medical images while moving from a first medical image 2131 to a third medical image 2135 in one screen.

According to an exemplary embodiment, the display 130 may set a size of a second medical image 2133 displayed at a center portion of the screen to be greater than those of the first and third medical images 2131 and 2135.

Also, the display 130 of the medical image displaying apparatus 100 may display an indicator 2125 for indicating a number of the medical image that is currently displayed, on a lower end portion 2120 of a screen 2110.

In addition, in FIGS. 20 and 21, the medical image displaying apparatus 100 displays the medical images while moving over the medical images arranged in a predetermined direction within the screen, but is not limited thereto. In an exemplary embodiment, as shown in FIG. 22, the medical image displaying apparatus 100 displays a first medical image 2240 included in a plurality of medical images 2260, and after that, when receiving a user input 2230 for switching the medical image, the medical image displaying apparatus 100 may display a second medical image 2270 at a location where the first medical image 2240 is displayed.

Figure 23:
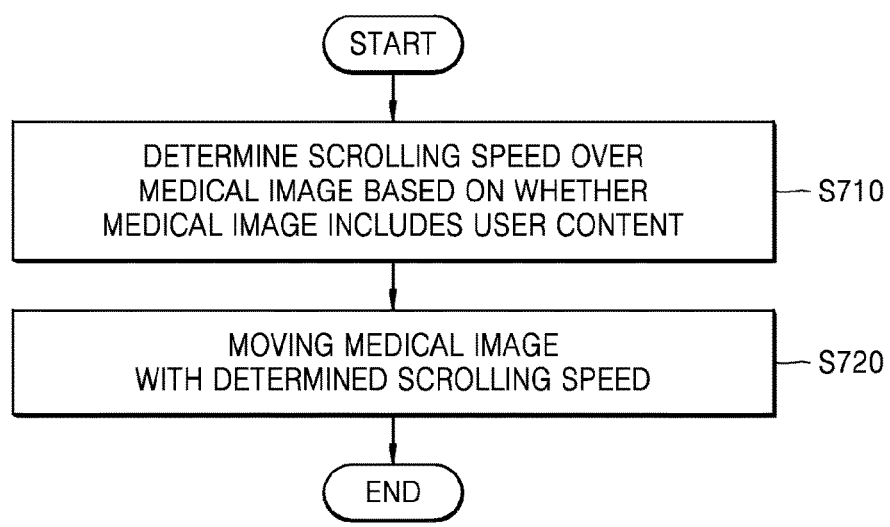
FIG. 23 is a flowchart of a method, in which a medical image displaying apparatus changes a switching speed, based on whether a medical image includes user content.

FIG. 23 is a flowchart of a method, in which the medical image displaying apparatus 100 changes the switching speed, based on whether the medical image includes user content.

Figure 24A:
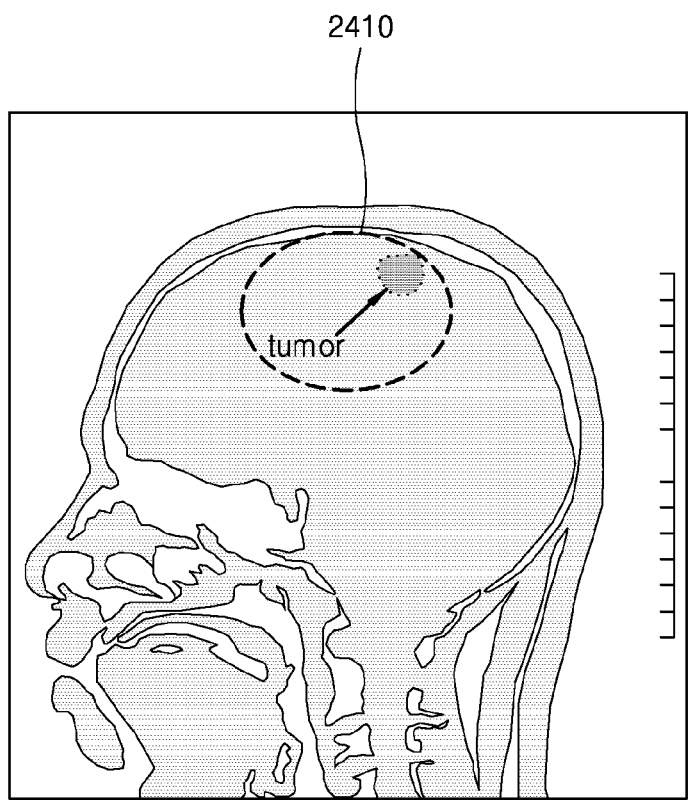
FIGS. 24A, 24B, and 24C are diagrams showing examples of an annotation, a marker, and an ROI included in medical images.
Figure 24B:
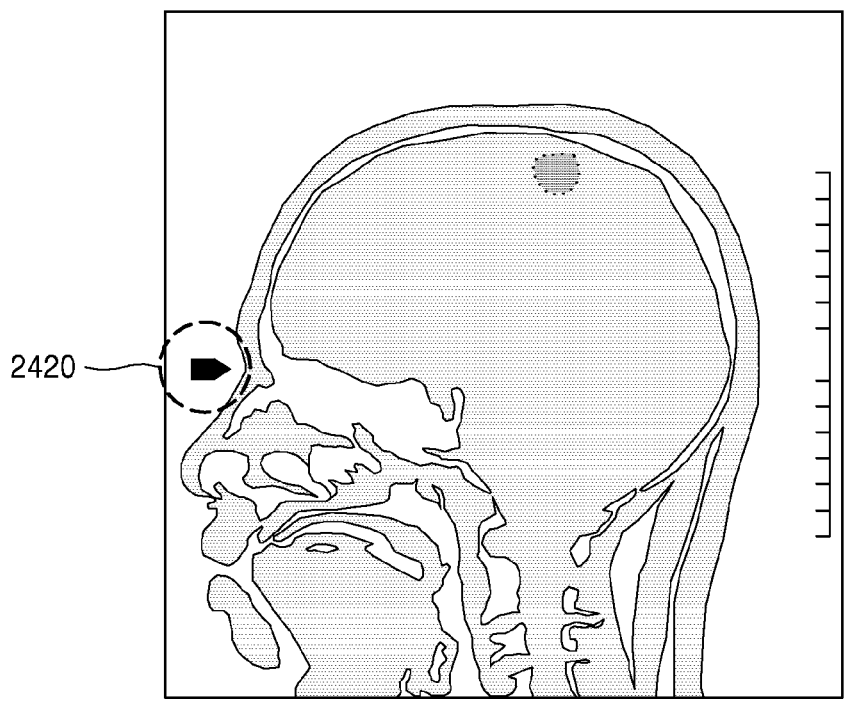
Figure 24C:
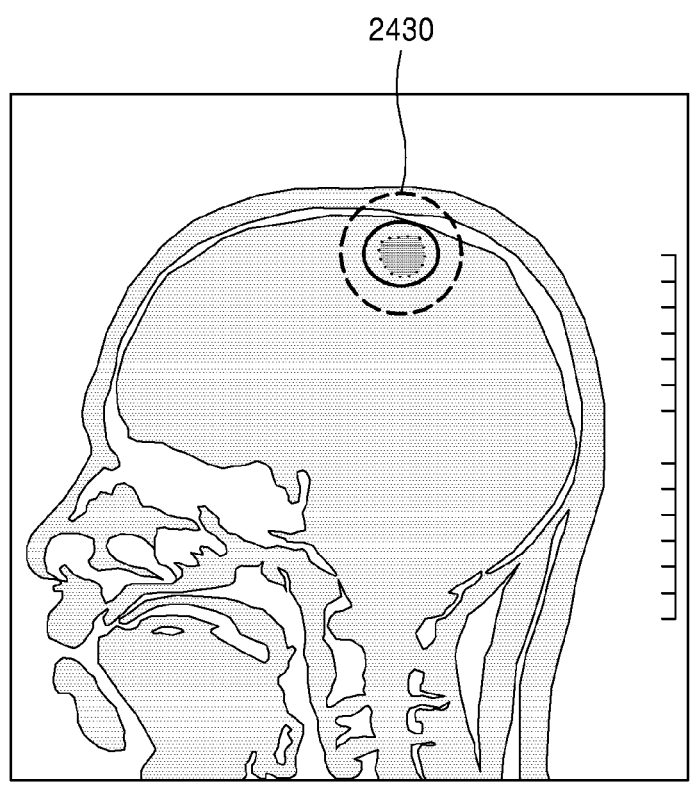

Referring to FIG. 23, the medical image displaying apparatus 100 may determine a switching speed of each medical image, based on whether each of the plurality of medical images includes user content (operation S710). As shown in FIGS. 24A, 24B, and 24C, the user content may include an annotation 2410, a marker 2420, and an ROI 2430. When the medical image includes the user content, the medical image displaying apparatus 100 may reduce a switching speed between the medical images.

Also, the medical image displaying apparatus 100 may determine a switching speed of each medical image, based on a type of the user content included in each medical image.

As shown in FIG. 25, the medical image displaying apparatus 100 may vary a reduction degree of the switching speed depending on the type of the user content. According to an exemplary embodiment, the switching speed may be expressed as a decimal between 0.0 and 1.0. For example, the switching speed 1.0 may denote that the medical images are switched according to a speed of scrolling over the plurality of medical images according to the user input, or according to a switching speed that is set in advance by the medical image displaying apparatus 100. For example, when the switching speed is 1.0, the medical image displaying apparatus 100 may display a first medical image among sixty medical images, for a preset one second on the screen of the medical image displaying apparatus 100. The switching speed 0.7 may denote that the medical images are switched 0.7 times slower than the speed of scrolling of the user input or 0.7 times slower than the switching speed that is set in advance by the medical image displaying apparatus 100. For example, when the switching speed for a first medical image is 0.5 and a preset display time is 1 second as above, the medical image displaying apparatus 100 may display the first medical image for two seconds.

For example, the medical image displaying apparatus 100 may set the switching speed of the medical images including annotation as 0.3. As another example, the medical image displaying apparatus 100 may set the switching speed of the medical images including a marker as 0.2. As another example, the medical image displaying apparatus 100 may set the switching speed of the medical images including the annotation and the marker as 0.1. I.e., the switching speed may depend on the information that the medical professional is predicted to review for a longer time, as determined by the controller 120.

Referring back to FIG. 23, the medical image displaying apparatus 100 may move each of the medical images with the switching speed that is determined (operation S720). Therefore, the switching speed with respect to the plurality of medical images may actively vary according to whether each of the plurality of medical images includes the user content.

Figure 26:
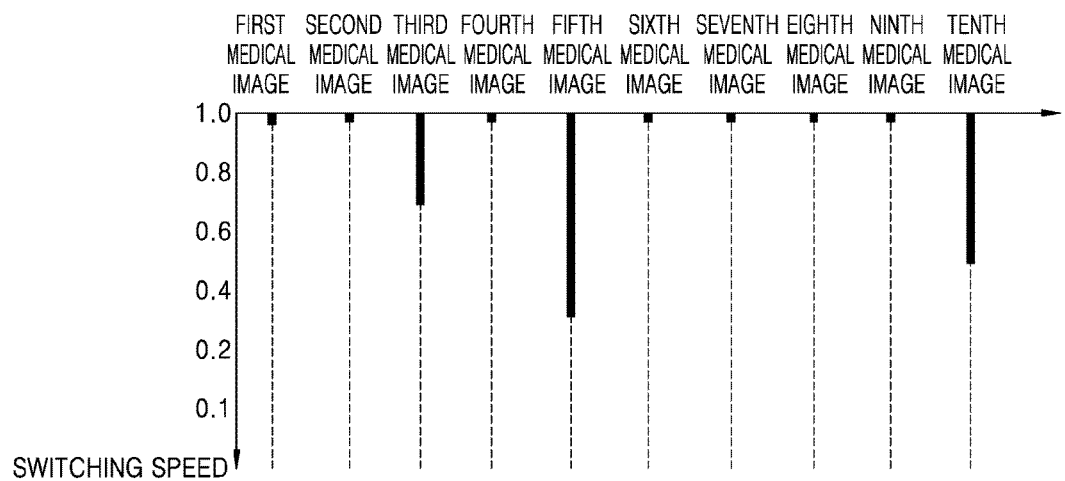
FIG. 26 is graph showing a switching speed of each of a plurality of medical images.

FIG. 26 is a graph showing a switching speed of each of the plurality of medical images. As shown in FIG. 26, each of the plurality of medical images may have different switching speed from those of the others.

Figure 27A:
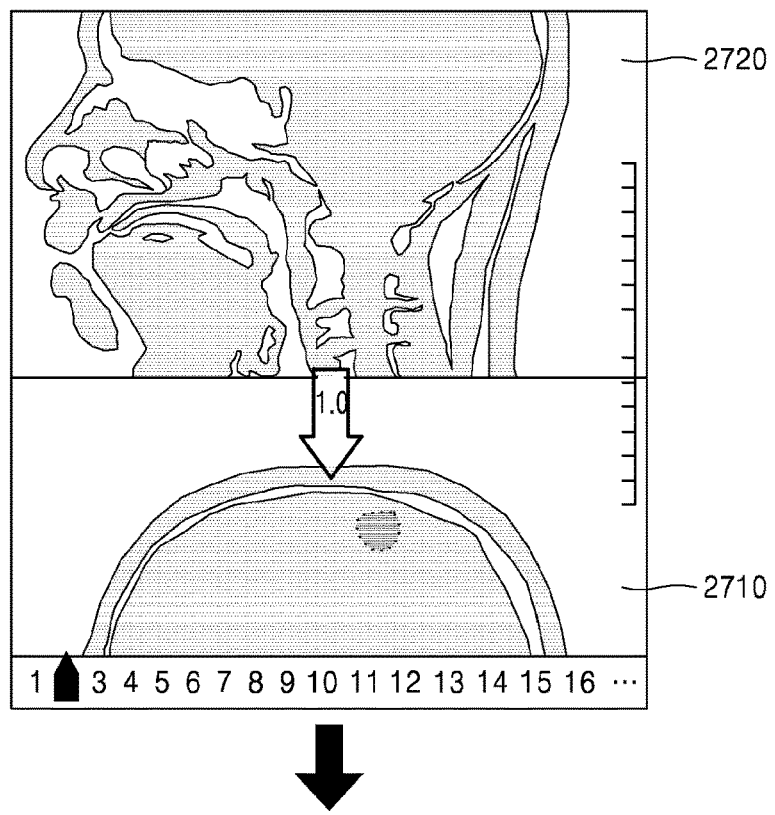
FIG. 27A is a diagram of an example of switching a first medical image to the second medical image shown in FIG. 26.
Figure 27A:
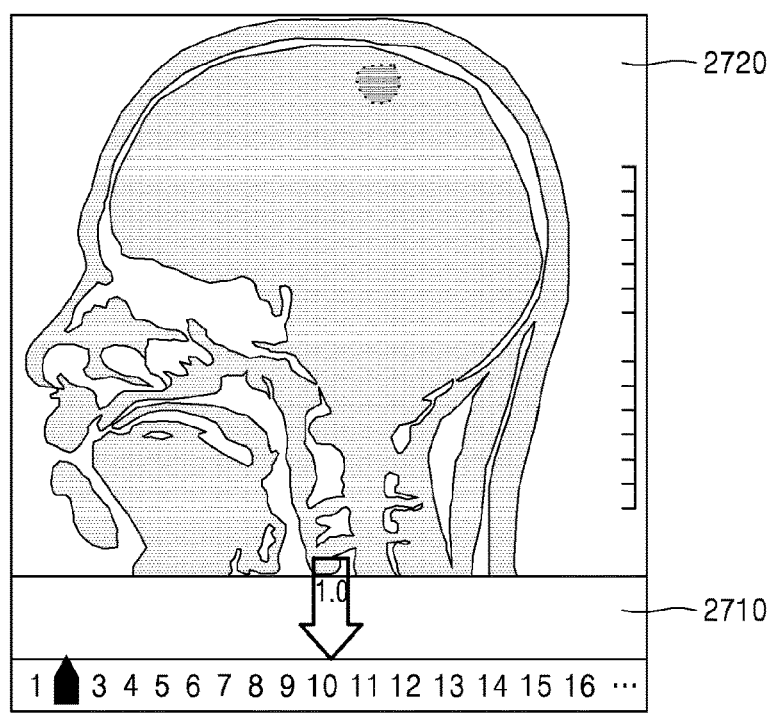
Figure 27B:
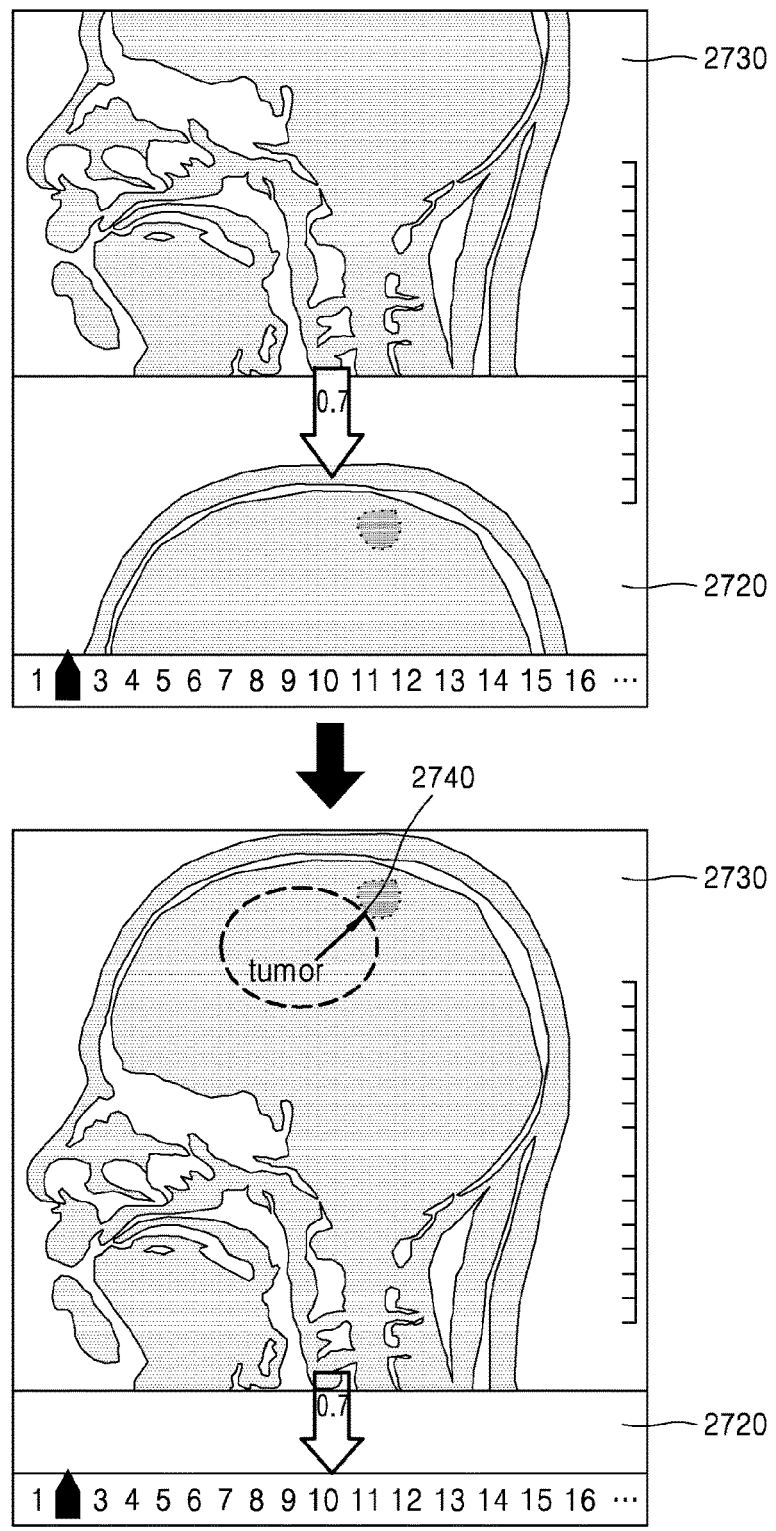
FIG. 27B is a diagram of an example of switching a second medical image to a third medical image shown in FIG. 26.

FIG. 27A is a diagram showing an example of switching the first medical image to the second medical image of FIG. 26, and FIG. 27B is a diagram showing an example of switching the second medical image to a third medical image of FIG. 26.

Referring to FIGS. 26 and 27A, the first medical image 2710 may be switched to a second medical image 2720 with a switching speed that is set in advance by the medical image displaying apparatus 100 (that is, 1.0). However, referring to FIGS. 26 and 27B, since a third medical image 2730 includes an annotation 2740, the controller 120 of the medical image displaying apparatus 100 may reduce the switching speed of the third medical image 2730. Therefore, the display 130 of the medical image displaying apparatus 100 may display the medical image while scrolling over the screen 0.7 times slower than the switching speed set in advance by the medical image displaying apparatus 100, from a point when the third medical image 2730 appears on the screen. For example, the switching speed of other medical image or images that are displayed on the screen before or after the third medical image 2730 may be adjusted to reflect the reduced switching speed of the third medical image 2730. I.e., one or some of the other images may be displayed for a shorter time while the third medical image 2730 may be displayed for a longer time.

Figure 28A:
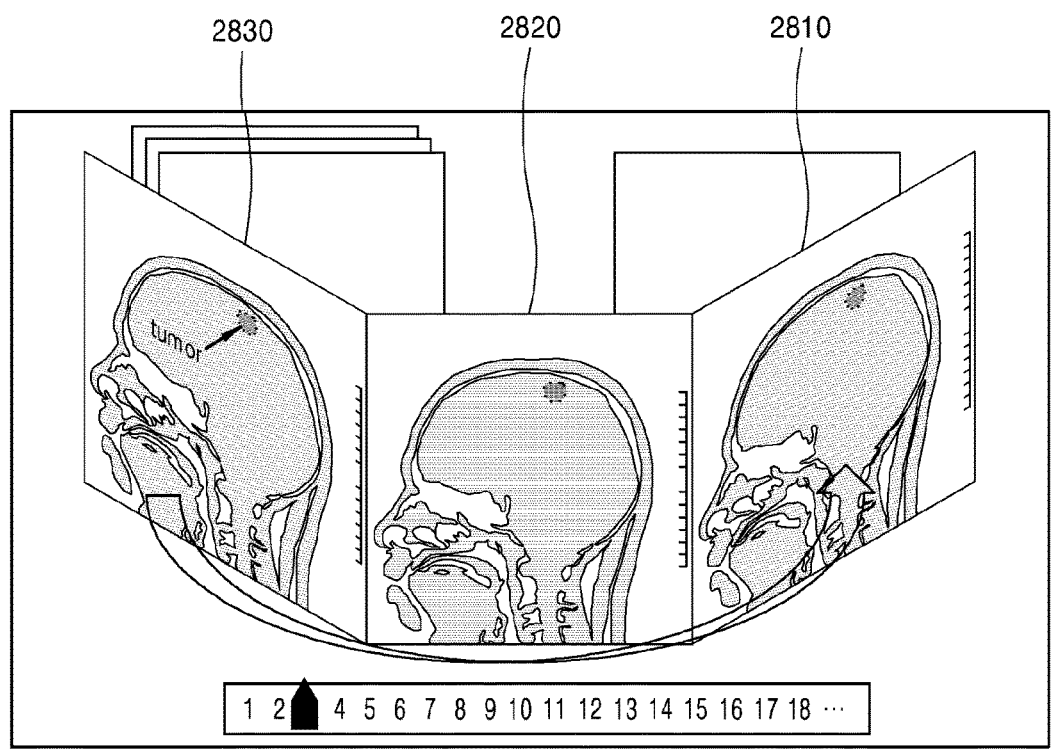
FIG. 28A is a diagram of another example of switching a first medical image to a second medical image of FIG. 26.
Figure 28B:
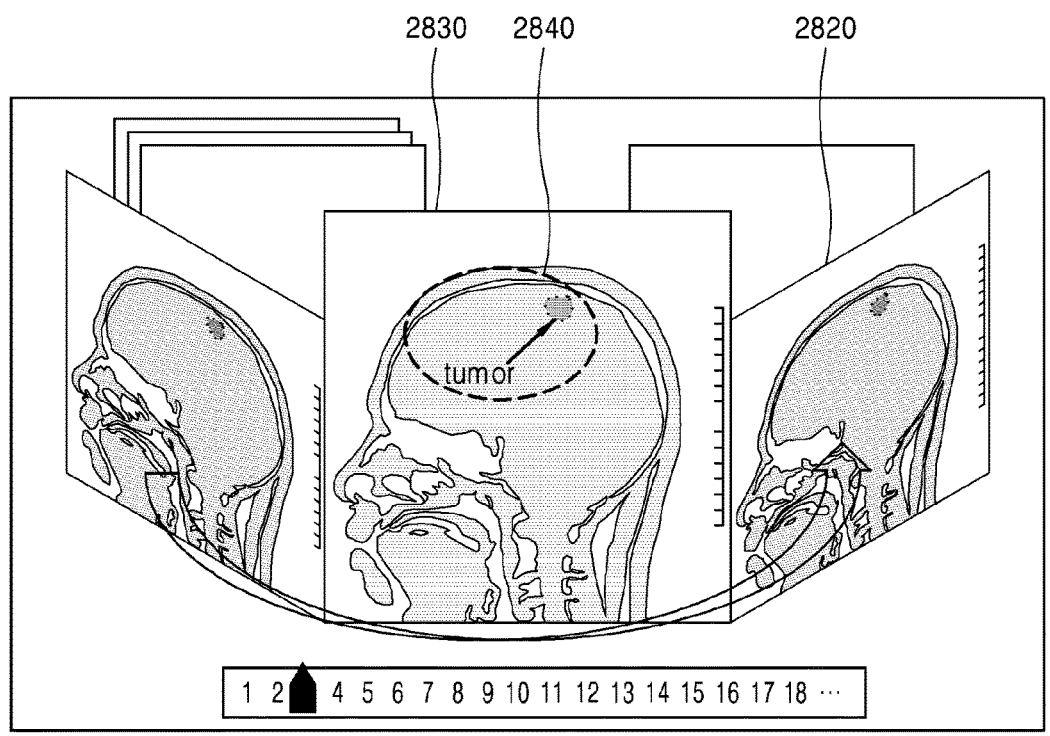
FIG. 28B is a diagram of another example of switching a second medical image to a third medical image of FIG. 26.

FIG. 28A is a diagram of another example of switching the first medical image to the second medical image of FIG. 26, and FIG. 28B is a diagram of another example of switching the second medical image to the third medical image of FIG. 26.

Referring to FIGS. 26 and 28A, a first medical image 2810 may be scrolled with a switching speed set in advance by the medical image displaying apparatus 100 (that is, 1.0) to be switched to the second medical image 2820.

Referring to FIGS. 26 and 28B, a third medical image 2830 including an annotation 2840 may be switched based on a switching speed reduced more (for example, a reduction by 0.7) than the switching speeds of the first and second medical images 2810 and 2820. That is, the third medical image 2830 including an annotation 2840 may be displayed for a longer time as compared to the first and second medical images 2810 and 2820. Also, according to an exemplary embodiment, the medical image displaying apparatus 100 may enlarge and display the third medical image 2830 when the third medical image 2830 is located at a center portion of the screen.

As described above, the medical image displaying apparatus 100 may control the medical images including the user content to be exposed on the screen for a longer time period than the other medical images, so as to increase user's accessibility to the medical image including the user content.

Figure 29:
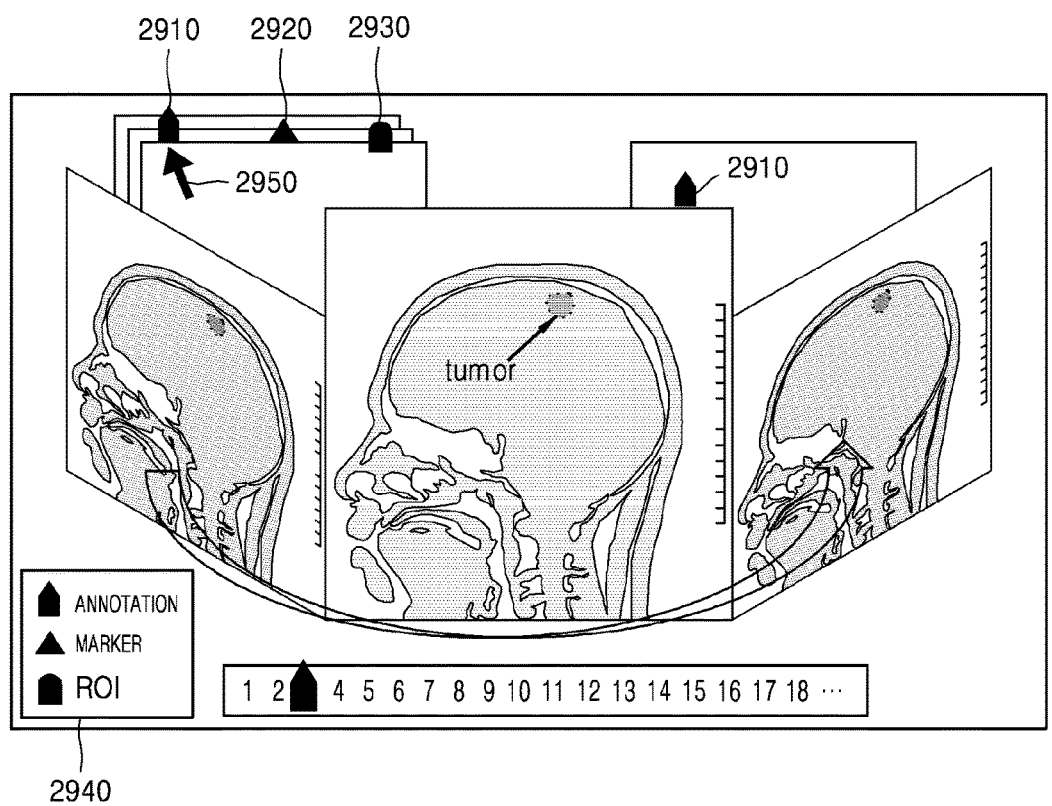
FIG. 29 is a diagram of an example, in which a medical image displaying apparatus expresses user content included in a medical image.

FIG. 29 is a diagram of an example, in which the medical image displaying apparatus 100 expresses user content included in a medical image.

Referring to FIG. 29, the display 130 of the medical image displaying apparatus 100 may display indicators 2910, 2920, and 2930 with respect to medical images including user content. The indicators 2910, 2920, and 2930 may have different shapes or colors according to types of the user content. Also, the medical image displaying apparatus 100 may display information 2940 about the user content and the indicators.

According to an exemplary embodiment, the user interface 110 of the medical image displaying apparatus 100 may receive a user input 2950 for selecting the indicator 2910, 2920, or 2930. The medical image displaying apparatus 100 may provide medical images including a selected indicator 2910, among the plurality of medical images. In addition, as described above, when the cursor approaches the indicators 2910, 2920, and 2930, the velocity of the cursor may increase.

Figure 30:
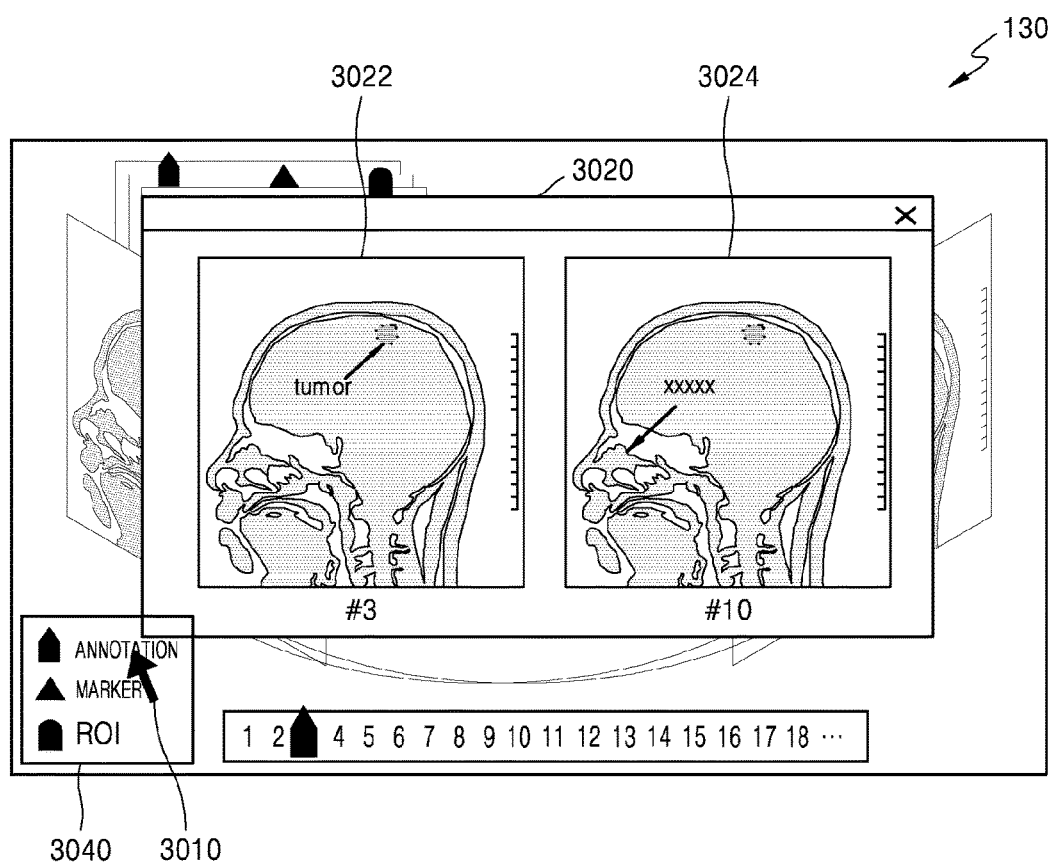
FIG. 30 is a diagram of an example, in which a medical image displaying apparatus searches for a medical image including certain user content among a plurality of medical images.

FIG. 30 is a diagram of an example, in which the medical image displaying apparatus 100 searches for a medical image including certain user content among a plurality of medical images.

Referring to FIG. 30, the information 2940 about the user content and the indicators may function as a search GUI for searching for medical images including certain user content. For example, the medical image displaying apparatus 100 may receive a user input 3010 about an indicator representing 'annotation' (e.g., an indicator like a bookmark) or text (e.g., "annotation") in the information 2940 about the user content and the indicators. The controller 120 of the medical image displaying apparatus 100 may search for medical images including annotation, among the plurality of medical images.

According to an exemplary embodiment, the controller 120 may index the plurality of medical images according to types of the user content, and store an index table. The controller 120 may search for the medical images including the annotation by using the index table.

Also, the display 130 of the medical image displaying apparatus 100 may display found medical images 3022 and 3024. For example, the display 130 may display the found medical images 3022 and 3024 via a popup window 3020.

As described above, the medical image displaying apparatus 100 may provide a way of easily accessing the medical images including certain user content. Also, the medical image displaying apparatus 100 provides the found medical images through the popup window 3020 so that the user may easily return to a previous screen.

Figure 31:
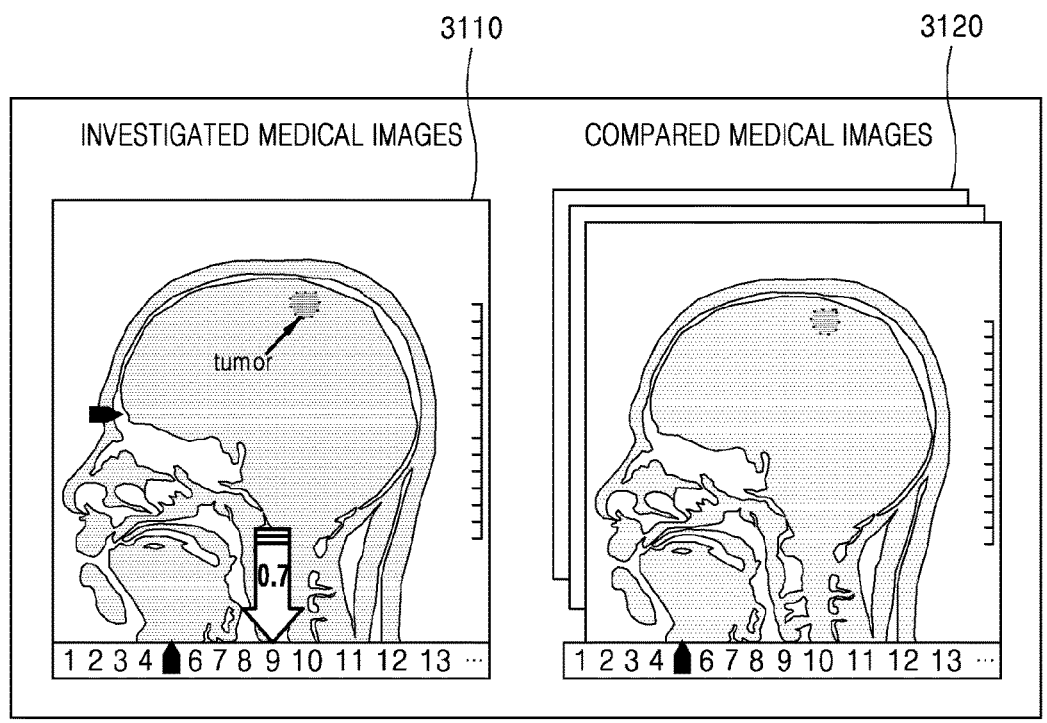
FIG. 31 is a diagram of an example, in which a medical image displaying apparatus may compare medical images that are included in different sets of a plurality of medical images and display the medical images.

FIG. 31 is a diagram of an example, in which the medical image displaying apparatus 100 may compare medical images that are included in different sets of a plurality of medical images and display the medical images.

Referring to FIG. 31, the medical image displaying apparatus 100 may display a first set of medical images 3110 and a second set of medical images 3120. For example, when receiving a user input, the medical image displaying apparatus 100 switches medical images included in the first set of medical images 3110 (hereinafter, referred to as "investigated medical images"), and then, medical images included in the second set of medical images 3120 (hereinafter, referred to as "compared medical images") may be switched automatically to be compared with the investigated medical images 3110. The compared medical images 3120 may be a plurality of medical images that are relevant to the investigated medical images 3110. For example, the investigated medical images 3110 and the compared medical images 3120 may be obtained from the same volume in the same object at different points of time. As another example, the investigated medical images 3110 and the compared medical images 3120 may be obtained from different volumes in the same object. As another example, the investigated medical images 3110 and the compared medical images 3120 may be obtained by applying different protocols to the same volume in the same object. However, this is not limited thereto.

According to an exemplary embodiment, when the medical image displaying apparatus 100 receives a user input, the medical image displaying apparatus 100 may display the medical images that are respectively included in the investigated medical images 3110 and the compared medical images 3120 on a same screen or different screens with the same switching speed.

As another example, when receiving the user input, the medical image displaying apparatus 100 displays the investigated medical images 3110 while switching the images, and then, switches the compared medical images 3120 in predetermined cases. For example, the medical image displaying apparatus 100 may switch the compared medical images 3120 only when the investigated medical images 3110 including user content are displayed. When medical images including the user content among the investigated medical images 3110 are displayed, the medical image displaying apparatus 100 may display medical images corresponding to the medical images including the user content, among the compared medical images 3120 (e.g., medical images having the same scanning order as those of the medical images including the user content).

Figure 32:
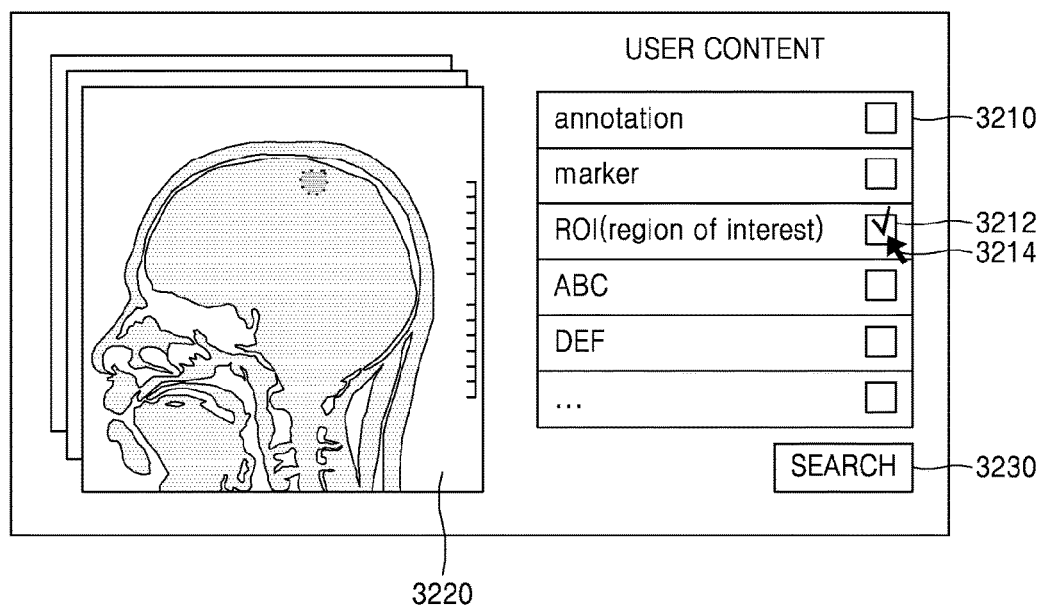
FIGS. 32 and 33 are diagrams of examples, in which a medical image displaying apparatus searches for medical images including certain user content among a plurality of medical images.
Figure 33:
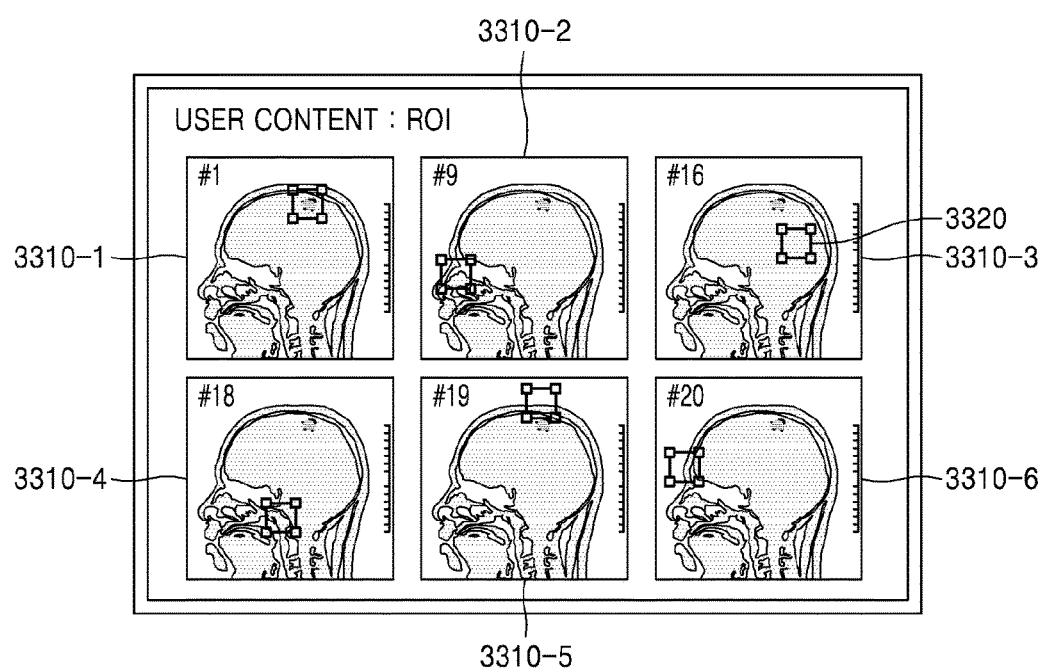

FIGS. 32 and 33 are diagrams of examples, in which the medical image displaying apparatus 100 searches for medical images including certain user content among a plurality of medical images.

According to an exemplary embodiment, the medical image displaying apparatus 100 may extract medical images including certain user content among the plurality of medical images, and may provide extracted medical images to the user. For example, the plurality of medical images may be relevant with each other. For example, the plurality of medical images may be a set of slices images obtained from a predetermined volume of an object. As another example, the plurality of medical images may be a set of medical images that are defined to be relevant with each other by the user. Also, the user content may be content generated by the user or content utilized by the user, and may include, for example, annotations, markers, and ROIs included in the medical images.

As shown in FIG. 32, according to an exemplary embodiment, the medical image displaying apparatus 100 may display a list 3210 of user content included in a plurality of medical images 3220. The medical image displaying apparatus 100 may receive a user input for selecting at least one from the list 3210 including the user content. According to an exemplary embodiment, the medical image displaying apparatus 100 provides check boxes corresponding to each piece of the user content, and receives a user input for selecting at least one of the check boxes. For example, the medical image displaying apparatus 100 may receive a user input 3214 for selecting a check box 3212 corresponding to the ROI from the list 3210 of the user content. After that, when a user input with respect to a 'search' button image 3230 is transmitted from the user, the medical image displaying apparatus 100 may extract medical images including the ROI selected from the list 3210 of the user content. In FIG. 32, the list 3210 of the user content is represented to include the check boxes, but is not limited thereto. That is, the medical image displaying apparatus 100 may provide various GUIs for receiving selection of predetermined user content from the user.

According to an exemplary embodiment, the medical image displaying apparatus 100 may display medical images 3310-1, 3310-2, 3310-3, 3310-4, 3310-5, and 3310-6 including the ROI 3320, among the plurality of medical images 3220, as shown in FIG. 33. The medical images 3310-1 to 3310-6 including the ROI may be arranged on the screen of the medical image displaying apparatus 100 in a time order of scanning the medical images 3310-1 to 3310-6, or may be arranged in an order of the number of ROIs included in each of the medical images. That is, although the medical images with only one ROI 3320 are illustrated, the medical images 3310-1 to 3310-6 may have a greater number of ROIs.

Figure 34:
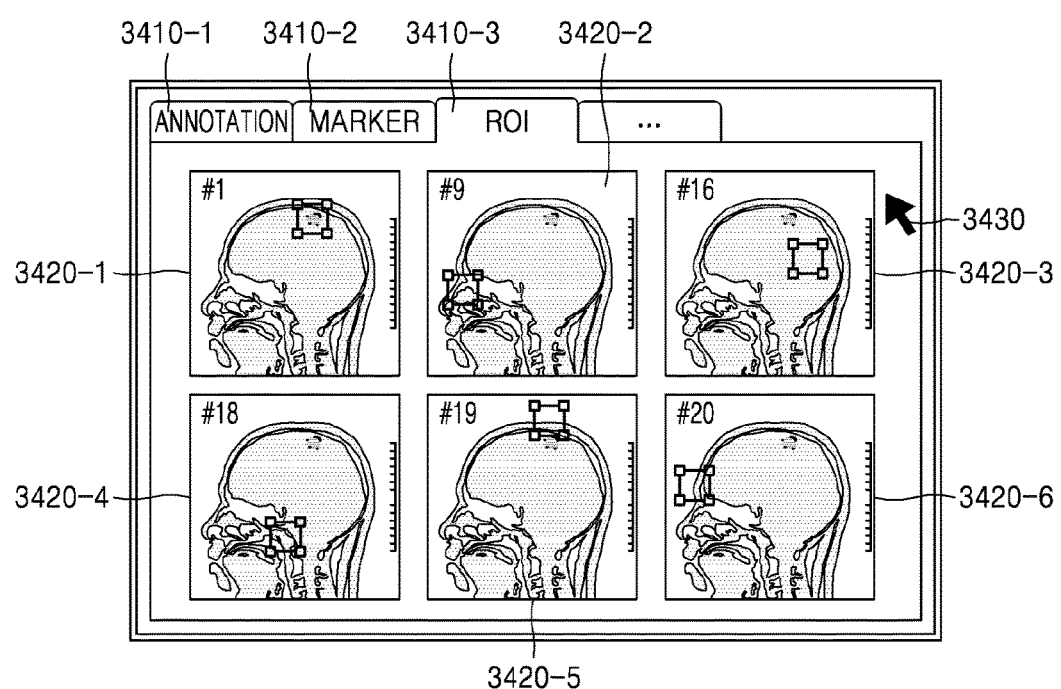
FIG. 34 is a diagram of an example, in which a medical image displaying apparatus provides medical images included in a plurality of medical images according to types of user content.

FIG. 34 is a diagram of an example, in which the medical image displaying apparatus 100 provides medical images included in a plurality of medical images according to types of user content.

Referring to FIG. 34, the medical image displaying apparatus 100 may display a plurality of templates 3410-1 to 3410-3 providing lists of medical images including certain user content. For example, the medical image displaying apparatus 100 may display the template 3410-3 on the top including a list of medical images 3420-1, 3420-2, 3420-3, 3420-4, 3420-5, and 3420-6 including ROIs. As another example, the medical image displaying apparatus 100 may display a template 3410-2 including a list of medical images including markers or a template 3410-3 including a list of medical images including annotations.

Also, the medical image displaying apparatus 100 may display a cursor 3430 moving in the screen of the medical image displaying apparatus 100 so that one of the plurality of templates 3410-1 to 3410-3 or one of the list of the medical images included in a selected template may be selected, and may receive a user input for moving the cursor 3430. The speed of the cursor may be adjusted as described above.

As described above, the medical image displaying apparatus 100 may provide a way of easily accessing medical images including the user content.

Figure 35:
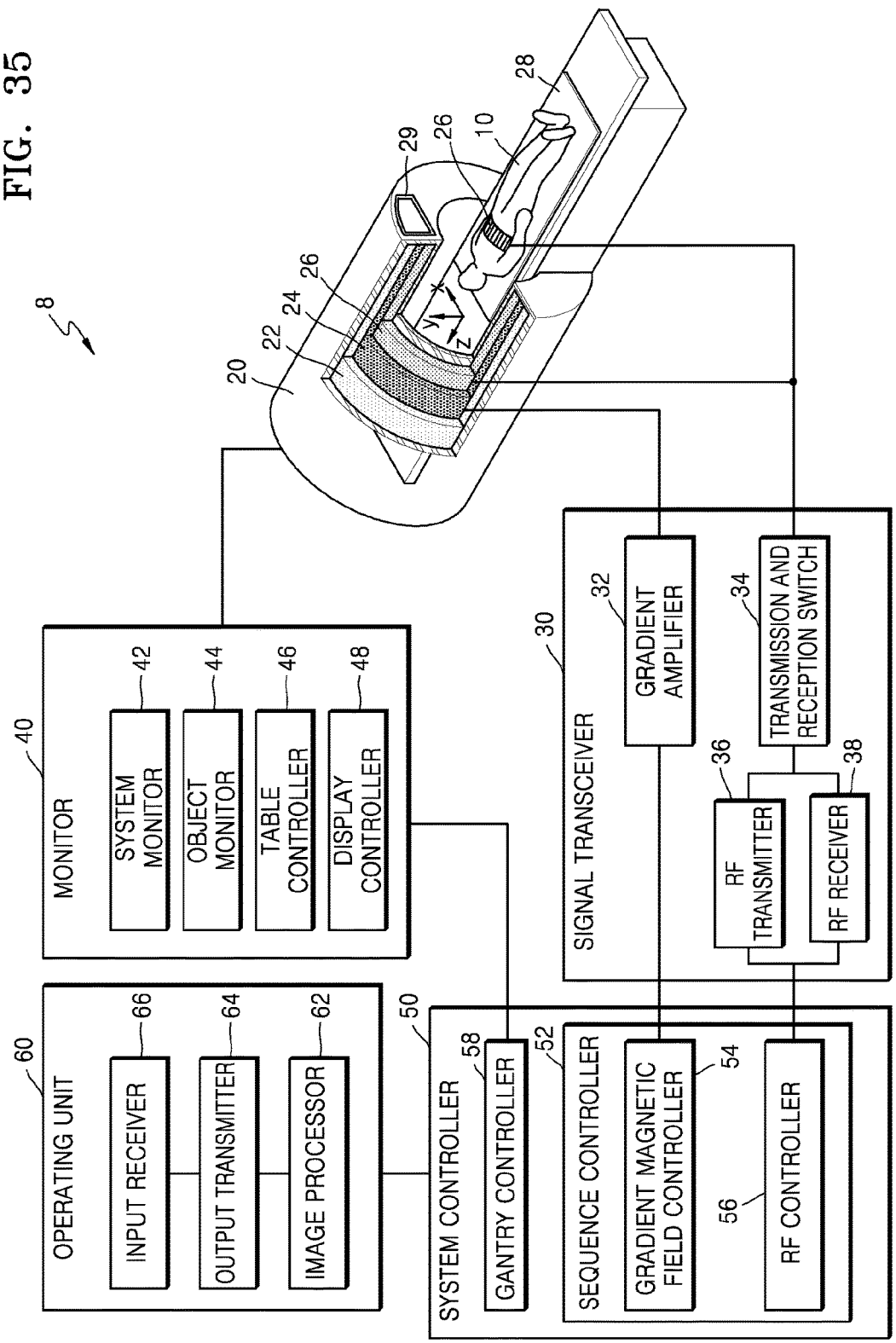
FIG. 35 is a schematic diagram illustrating an example structure of an MRI system.

FIG. 35 is a block diagram illustrating an example structure of an MRI system 8. Referring to FIG. 35, the MRI system may include a gantry 20, a signal transceiver 30, a monitor 40, a system controller 50, and an operating unit 60.

The gantry 20 prevents external emission of electromagnetic waves generated by a main magnet 22, a gradient coil 24, and an RF coil or coils 26. A magnetostatic field and a magnetic field gradient are formed in a bore of the gantry 20, and an RF signal is emitted toward a body 10.

The main magnet 22, the gradient coil 24, and the RF coil 26 may be arranged in a predetermined direction of the gantry 20. The predetermined direction may be a coaxial cylinder direction. The body 10 may be disposed on a table 28 that is capable of being inserted into a cylinder along a horizontal axis of the cylinder.

The main magnet 22 generates a magnetostatic field for aligning magnetic dipole moments of atomic nuclei of the body 10 in a constant direction. A precise and accurate MR image of the body 10 may be obtained due to a magnetic field generated by the main magnet 22 being strong and uniform.

The gradient coil 24 includes X, Y, and Z coils for generating magnetic field gradients in X-, Y-, and Z-axis directions. The gradient coil 24 may provide location information of each region of the body 10 by differently inducing resonance frequencies according to the regions of the body 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, in order to transit an atomic nucleus from a low energy state to a high energy state, the RF coil 26 may generate and apply an electromagnetic wave signal that is an RF signal corresponding to a type of the atomic nucleus, to the body 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei included in the body 10.

The RF coil 26 may be a single RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may include a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the body, such as a head RF coil, a chest RF coil, a leg RF coil, a neck RF coil, a shoulder RF coil, a wrist RF coil, and/or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil.

The RF coil 26 may be an RF coil having various numbers of channels, such as 16 channels, 32 channels, 72 channels, and 144 channels.

The gantry 20 may further include a first display 29 disposed outside the gantry 20 and a second display (not shown) disposed inside the gantry 20. The gantry 20 may provide predetermined information to the user or the body 10 through the first display 29 and the second display respectively disposed outside and inside the gantry 20.

The signal transceiver 30 may control the magnetic field gradient formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal to the gradient coil 24 for generating a magnetic field gradient under the control of a gradient magnetic field controller 54. By controlling the pulse signal supplied from the gradient amplifier 32 to the gradient coil 24, magnetic field gradients in X-, Y-, and Z-axis directions may be synthesized.

The RF transmitter 36 and the RF receiver 38 may drive the RF coil 26. The RF transmitter 36 may supply an RF pulse in a Larmor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the body 10 through the RF coil 26 during a transmission mode, and receive the MR signal from the body 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 may include a system monitor 42, an object monitor 44, a table controller 46, and a display controller 48.

The system monitor 42 may monitor and control a state of the magnetostatic field, a state of the magnetic field gradient, a state of the RF signal, a state of the RF coil 26, a state of the table 28, a state of a device measuring body information of the body 10, a power supply state, a state of a thermal exchanger, and a state of a compressor.

The monitor 44 monitors a state of the body 10. In detail, the monitor 44 may include a camera for observing a movement or position of the body 10, a respiration measurer for measuring the respiration of the body 10, an electrocardiogram (ECG) measurer for measuring the heart activity of the body 10, or a temperature measurer for measuring a temperature of the body 10.

The table controller 46 controls a movement of the table 28 where the body 10 is positioned. The table controller 46 may control the movement of the table 28 according to a sequence control of a sequence controller 52. For example, during moving imaging of the body 10, the table controller 46 may continuously or discontinuously move the table 28 according to the sequence control of the sequence controller 52, and thus the body 10 may be imaged in a field of view (FOV) larger than that of the gantry 20.

The display controller 48 controls the first display 29 disposed outside the gantry 20 and the second display disposed inside the gantry 20. In detail, the display controller 48 may control the first display 29 and the second display to be on or off, and may control a screen image to be output on the first display 29 and/or the second display. Also, when a speaker is located inside or outside the gantry 20, the display controller 48 may control the speaker to be on or off, or may control sound to be output via the speaker.

The system controller 50 may include the sequence controller 52 for controlling a sequence of signals transmitted to the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. For example, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system controller 50 to transmit pulse sequence information while controlling an overall operation of the MRI system.

The operating unit 60 may include an image processor 62 for receiving and processing the MR signal received by the RF receiver 38, an output transmitter 64, and an input receiver 66.

The image processor 62 may process the MR signal received from the RF receiver 38 so as to generate MR image data of the body 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space (for example, also referred to as a Fourier space or a frequency space) of a memory, and rearrange the digital data into image data via 2D or 3D Fourier transformation.

If needed, the image processor 62 may perform a composition process or difference calculation process on the image data. The composition process may include an addition process on a pixel or a maximum intensity projection (MIP) process. The image processor 62 may store the rearranged image data and the image data on which a composition process or a difference calculation process is performed, in a memory (not shown) or an external server.

The image processor 62 may perform any of the signal processes on the MR signal in parallel. For example, the image processor 62 may perform a signal processing on a plurality of MR signals received by a multi-channel RF coil in parallel so as to rearrange the plurality of MR signals into image data.

According to an exemplary embodiment, the image processor 62 may include the controller 120 of FIG. 1.

The output transmitter 64 may output image data generated or rearranged by the image processor 62 to the user. The output transmitter 64 may also output information required for the user to manipulate the MRI system, such as a GUI, user information, or body information. The output transmitter 64 may be a speaker, a printer, a CRT display, an LCD, a PDP, an OLED display, an FED, an LED display, a VFD, a DLP display, a FPD, a 3D display, a transparent display, or any one of other appropriate output devices known to one of ordinary skill in the art.

According to an exemplary embodiment, the output transmitter 64 may include the display 130 of FIG. 1.

The user may input body information, parameter information, a scan condition, a pulse sequence, or information about image composition or difference calculation by using the input receiver 66. The input receiver 66 may be a keyboard, a mouse, a track ball, a voice recognizer, a gesture recognizer, a touch screen, or any one of other various input devices known to one of ordinary skill in the art.

According to an exemplary embodiment, the input receiver 66 may include the user interface 110 of FIG. 1.

The signal transceiver 30, the monitor 40, the system controller 50, and the operating unit 60 are separate components in FIG. 35, but the respective functions of the signal transceiver 30, the monitor 40, the system controller 50, and the operating unit 60 may be performed by a single component or another component. For example, the image processor 62 converts the MR signal received from the RF receiver 38 into a digital signal in FIG. 35, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating unit 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitor 40, the system controller 50, and the operating unit 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any of other various communication methods known to one of ordinary skill in the art.

Figure 36:
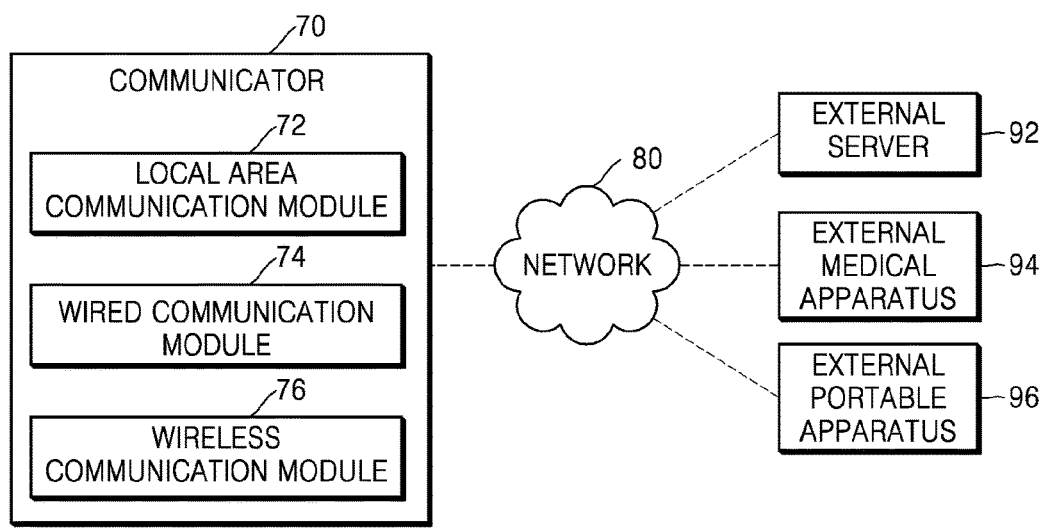
FIG. 36 is a block diagram illustrating an example structure of a communicator according to an exemplary embodiment.

FIG. 36 is a block diagram illustrating an example structure of a communicator 70 according to an exemplary embodiment. Referring to FIG. 36, the communicator 70 may be connected to at least one among the gantry 20, the signal transceiver 30, the monitor 40, the system controller 50, and the operating unit 60 of FIG. 35.

The communicator 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 36, the communicator 70 may be connected to a network 80 by wire or wirelessly to communicate with a server 92, a medical apparatus 94, or a portable device 96.

In detail, the communicator 70 may transmit and receive data related to the diagnosis of a patient through the network 80, and may also transmit and receive a medical image captured by the medical apparatus 94, such as a CT apparatus, an MRI apparatus, or an X-ray apparatus. The communicator 70 may receive a diagnosis history or a treatment schedule of the patient from the server 92 and use the same to diagnose the patient. The communicator 70 may perform data communication with the server 92 or the medical apparatus 94 in a hospital, and also with the portable device 96, such as a mobile phone, a personal digital assistant (PDA), or a laptop of a doctor or patient.

Also, the communicator 70 may transmit information about a malfunction of the MRI system 8 or about a medical image quality to a user through the network 80, and receive a feedback regarding the information from the user.

The communicator 70 may include at least one component enabling communication with an external apparatus.

For example, the communicator 70 may include a local area communication module 72, a wired communication module 74, and a wireless communication module 76. The local area communication module 72 refers to a module for performing local area communication with an apparatus within a predetermined distance. Examples of local area communication technology according to an exemplary embodiment include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication module 74 refers to a module for performing communication by using an electrical signal or an optical signal. Examples of wired communication technology according to an exemplary embodiment include wired communication techniques using a paired cable, a coaxial cable, and an optical fiber cable, and other appropriate wired communication techniques.

The wireless communication module 76 transmits and receives a wireless signal to and from at least one among a base station, an external apparatus, and a server in a mobile communication network. For example, the wireless signal may be a voice call signal, a video call signal, or data in any one of various formats according to transmission and reception of a text and/or multimedia message.

The above-described exemplary embodiments may be written as computer programs and may be implemented in computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

Although a few exemplary embodiments have been shown and described, it would be appreciated by those skilled in the art that changes may be made in the exemplary embodiments without departing from the principles and spirit of the disclosure, the scope of which is defined in the claims and their equivalents.

What is claimed is:

1. A medical imaging apparatus comprising:
   a processor;
   a user input receiver coupled to the processor and configured to receive a user input with respect to a cursor; and
   a display having a screen configured to display a medical image, a plurality of graphical user interfaces (GUIs), and the cursor on the medical image based on the user input, each of the plurality of GUIs being a graphical object, which is imposed as an overlay on the medical image and is selectable and movable with the cursor,
   wherein the processor is configured to move the cursor based on the user input and change a velocity of the cursor based on sensitivity information of the cursor that is determined based on at least one from among a distance between a first GUI from among the plurality of GUIs and the cursor and crowdedness of the plurality of GUIs.

2. The medical imaging apparatus of claim 1, wherein the crowdedness of the plurality of GUIs is determined based on distances among the plurality of GUIs.

3. The medical imaging apparatus of claim 1, wherein the processor is further configured to:
generate a new GUI,
control the display to display the new GUI overlaid on the medical image, and
update the sensitivity information of the cursor based on the location of the first GUI and a location of the new GUI, with respect to one another.

4. The medical imaging apparatus of claim 3, wherein the first GUI and the new GUI has a first area surrounding the first GUI and the new GUI, respectively,
a sensitivity of the cursor is preset, as the sensitivity information of the cursor, to a first value corresponding to the first area, and
the processor is further configured to:
determine the velocity of the cursor based on the first value of the sensitivity of the cursor when the cursor is moved, based on the user input, in an area where the first area of the first GUI and the first area of the new GUI do not overlap, and
increase the first value of the sensitivity of the cursor to a second value, when the first area of the first GUI overlaps the first area of the new GUI, and to determine the velocity of the cursor based on the second value of the sensitivity of the cursor when the cursor is moved, based on the user input, in an area where the first area of the first GUI overlaps the first area of the new GUI.

5. The medical imaging apparatus of claim 1, wherein the first GUI is a property changing GUI configured to change a property of the medical image,
the user input receiver is further configured to receive a user selection input for selecting the property changing GUI to change the property of the medical image, and
the processor is further configured to change a value of the property of the medical image to a different property value, based on the user selection input received through the property changing GUI.

6. The medical imaging apparatus of claim 1, wherein
the user input receiver is further configured to receive an input of a user via a key, and
the processor is further configured to select at least one of the plurality of GUIs that is located in a moving direction, in which the cursor is moved, based on the moving direction of the cursor when the key is input.

7. A medical image displaying method performed by a medical imaging apparatus, the medical image displaying method comprising:
receiving a user input with respect to a cursor;
displaying on a display screen a medical image and a plurality of graphical user interfaces (GUIs), each of the plurality of GUIs being a graphical object, which is imposed as an overlay on the medical image and is selectable and movable with the cursor;
displaying and moving the cursor based on the user input, on the medical image; and
controlling, by a processor of the medical imaging apparatus, a velocity of the cursor based on a sensitivity information of the cursor that is determined based on at least one from among a distance between a first GUI from among the plurality of GUIs and the cursor and a crowdedness of the plurality of GUIs.

8. The medical image displaying method of claim 7, wherein
the crowdedness of the plurality of GUIs is determined based on distances among the plurality of GUIs with respect to one another.

9. The medical image displaying method of claim 7, wherein the displaying the plurality of GUIs comprises generating a new GUI and displaying the new GUI overlaid on the medical image, and
the controlling the velocity of the cursor comprises changing the sensitivity information of the cursor based on the location of the first GUI and a location of the new GUI.

10. The medical image displaying method of claim 9, wherein each of the first GUI and the new GUI has a first area surrounding the first GUI and the new GUI, respectively,
a sensitivity of the cursor is preset, as the sensitivity information of the cursor, to a first value corresponding to the first area, and
the controlling the velocity of the cursor further comprises:
determining the velocity of the cursor based on the first value of the sensitivity of the cursor when the cursor is moved based on the user input in an area where the first area of the first GUI and the first area of the new GUI do not overlap, and
increasing the first value of the sensitivity of the cursor to a second value, when the first area of the first GUI overlaps the first area of the new GUI, and determining the velocity of the cursor based on the second value of the sensitivity of the cursor when the cursor is moved, based on the user input, in an area where the first area of the first GUI overlaps the first area of the new GUI.

11. The medical image displaying method of claim 7, wherein the first GUI is a property changing GUI configured to change a property of the medical image, and
the medical image displaying method further comprises:
receiving a user selection input for selecting the property changing GUI to change the property of the medical image; and
changing the property of the medical image to a different property value, based on the user selection input received through the property changing GUI.

12. The medical image displaying method of claim 7, wherein
the medical image displaying method further comprises:
receiving an input of a user via a key; and
selecting one of the plurality of GUIs located on a moving direction, in which the cursor is moved, based on the moving direction of the cursor when the key is input.

13. A non-transitory computer-readable recording medium having embodied thereon a program which, when executed by a computer system, causes the computer system to execute the medical image displaying method of claim 7.

14. The medical imaging apparatus of claim 1, wherein the plurality of GUIs is comprises at least one from among a window for setting a scanning parameter of the medical imaging apparatus and a line for setting a property for displaying the medical image, and
the window or the line is displayed to be overlapped on the medical image.

15. The medical imaging apparatus of claim 1, wherein the plurality of GUIs comprises at least one from among a GUI for setting a region of interest on the medical image, a GUI for setting a scanning area on the medical image, and a GUI for setting an angle of an object displayed on the medical image.

* * * * *